(12) United States Patent
Chen et al.

(10) Patent No.: US 10,604,462 B2
(45) Date of Patent: Mar. 31, 2020

(54) PROCESS FOR MAKING GAMMA-BRANCHED ALCOHOL

(71) Applicant: ExxonMobil Chemical Patents Inc., Baytown, TX (US)

(72) Inventors: Patrick C. Chen, Houston, TX (US); Kyle G. Lewis, Houston, TX (US)

(73) Assignee: ExxonMobil Chemical Patents Inc., Baytown, TX (US)

(*) Notice: Subject to any disclaimer, the term of this patent is extended or adjusted under 35 U.S.C. 154(b) by 0 days.

(21) Appl. No.: 15/988,604

(22) Filed: May 24, 2018

(65) Prior Publication Data

US 2019/0062242 A1    Feb. 28, 2019

Related U.S. Application Data

(60) Provisional application No. 62/551,005, filed on Aug. 28, 2017.

(51) Int. Cl.
*C07C 29/141* (2006.01)
*C07C 2/34* (2006.01)
*C07C 45/50* (2006.01)

(52) U.S. Cl.
CPC .......... *C07C 29/141* (2013.01); *C07C 2/34* (2013.01); *C07C 45/50* (2013.01); *C07C 2531/14* (2013.01); *C07C 2531/22* (2013.01)

(58) Field of Classification Search
CPC ...... C07C 29/141; C07C 2/34; C07C 2531/14
USPC ......................................................... 568/885
See application file for complete search history.

(56) References Cited

U.S. PATENT DOCUMENTS

| | | | |
|---|---|---|---|
| 3,652,655 A | 3/1972 | Fenton | |
| 4,658,708 A * | 4/1987 | Rastoin | A21C 15/002 |
| | | | 118/24 |
| 4,973,788 A | 11/1990 | Lin et al. | |
| 5,087,788 A | 2/1992 | Wu | |
| 5,625,106 A | 4/1997 | Marks et al. | |
| 8,119,850 B2 | 2/2012 | Fujikawa et al. | |
| 8,383,869 B2 | 2/2013 | De Kraker | |
| 8,748,361 B2 | 6/2014 | Wu et al. | |
| 2016/0017105 A1 | 1/2016 | Wu et al. | |
| 2017/0183595 A1 | 6/2017 | Ng et al. | |
| 2018/0119045 A1 | 5/2018 | Patil et al. | |

FOREIGN PATENT DOCUMENTS

| | | | |
|---|---|---|---|
| DE | 19653829 | 6/1998 | |
| EP | 1710225 | 10/2006 | |
| EP | 1710225 A1 * | 10/2006 | ............. C07C 17/16 |
| GB | 999725 | 7/1965 | |
| JP | 2004-077791 | 3/2004 | |
| JP | 2005-298443 | 10/2005 | |
| JP | 2005298443 A * | 10/2005 | |
| WO | 2014/004776 | 1/2014 | |
| WO | 2017/036755 | 3/2017 | |
| WO | 2017/116900 | 7/2017 | |

OTHER PUBLICATIONS

U.S. Appl. No. 15/904,629, filed Feb. 26, 2018 Lewis et al.

* cited by examiner

*Primary Examiner* — Deborah D Carr

(57) ABSTRACT

This disclosure relates to a process for making an alcohol product comprising a gamma-branched alcohol from a vinylidene olefin by hydroformylation.

25 Claims, 3 Drawing Sheets

PROCESS FOR MAKING GAMMA-BRANCHED ALCOHOL

PRIORITY

This application claims priority to and the benefit of U.S. Provisional Application No. 62/551,005, filed Aug. 28, 2017, and is incorporated herein by reference.

This disclosure relates to alcohols and processes for making the same. In particular, this disclosure relates to gamma-branched alcohols and processes for making the same.

BACKGROUND OF THE DISCLOSURE

Branched aliphatic primary alcohols, especially those having long carbon chains, have found use in many applications such as surfactants, solvents, wetting agents, solubilizing agents, emulsifiers, or as an intermediates for making derivatives such as esters and ethers that can be used as surfactants, solvents, wetting agents, solubilizing agents, emulsifiers, and lubricant base stocks or additives.

A specific type of branched aliphatic alcohols are Guerbet alcohols, which are beta-branched primary alcohols having the following general structure:

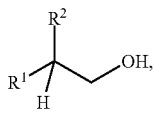

where $R^1$ and $R^2$ can be any hydrocarbyl group, preferably alkyl groups such as linear alkyl groups. Guerbet alcohols and derivatives thereof, such as esters thereof, have found use as lubricant base stocks. Guerbet alcohols can be produced by Guerbet reaction, in which two primary alcohol molecules condense to produce a beta-branched primary alcohol molecule and water.

Recently, industrial interests in gamma-branched alcohols having structures similar to Guerbet alcohols as follows have grown:

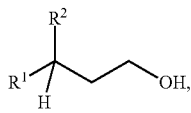

where $R^1$ and $R^2$ can be any hydrocarbyl group. Such gamma-branched alcohols cannot be produced via two molecules of primary alcohols.

U.S. Pat. No. 8,383,869 B2 discloses a process for making such gamma-branched alcohols from a terminal olefin including a first step of producing a vinylidene olefin dimer of the terminal olefin, followed by hydroformylation of the vinylidene olefin dimer. However, this patent teaches that in the hydroformylation process, multiple alcohol isomers will be produced. Because the isomers have the same molecular weight and similar molecular structure, it would be very difficult to produce one gamma-branched alcohol at high purity. JP2005-298443A discloses a similar process for making gamma-branched alcohols from alpha-olefin. While a high purity gamma-branched alcohol was reportedly produced in an example in this patent publication, the purity still has room for improvement. In addition, the overall yield of the gamma-branched alcohol product from the terminal olefin as disclosed in JP2005-298443A has room for improvement as well.

A high-purity gamma-alcohol product can be far more useful than a mixture of multiple alcohols having different molecular structures. This is especially true where the gamma-branched alcohol is used as a feed to produce a derivative thereof, and a high purity of the derivative is desired for its end application.

Thus, there is a need for a high purity gamma-branched alcohol products and a process for making high-purity gamma-branched alcohol products with a high yield.

This disclosure satisfy this and other needs.

SUMMARY OF THE DISCLOSURE

It has been found that, surprisingly and contrary to the teachings in U.S. Pat. No. 8,383,869, by using a Rh-containing carbonylation catalyst in combination with a phosphine compound, followed by hydrogenation, one can effect the hydroformylation of a vinylidene olefin with an overall selectivity toward gamma-branched alcohol at much higher level than reported in the prior art.

This disclosure relates to a process for making an alcohol product comprising a gamma-branched alcohol having a formula (F-I) below:

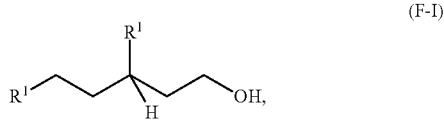

(F-I)

where each $R^1$ group, the same or different, is independently a C2-C28 linear or branched alkyl group, the process comprising the following steps: (I) providing a vinylidene feed comprising a vinylidene olefin having a formula (F-II) below:

(F-II)

where the $R^1$ groups correspond to the $R^1$ groups in formula (F-I) above; (II) contacting the vinylidene olefin with carbon monoxide and hydrogen in the presence of a carbonylation catalyst system comprising a rhodium-containing compound and a phosphine compound to obtain a carbonylation product mixture; and (III) contacting the carbonylation product mixture with hydrogen in the presence of a hydrogenation catalyst to produce an alcohol product comprising the gamma-branched alcohol, wherein: steps (II) and (III) combined have a selectivity of the vinylidene olefin toward the gamma-branched alcohol of at least 90%.

Further objects, features and advantages of this disclosure will be understood by reference to the following drawings and detailed description.

DETAILED DESCRIPTION OF THE DISCLOSURE

Definitions

Figure 1:
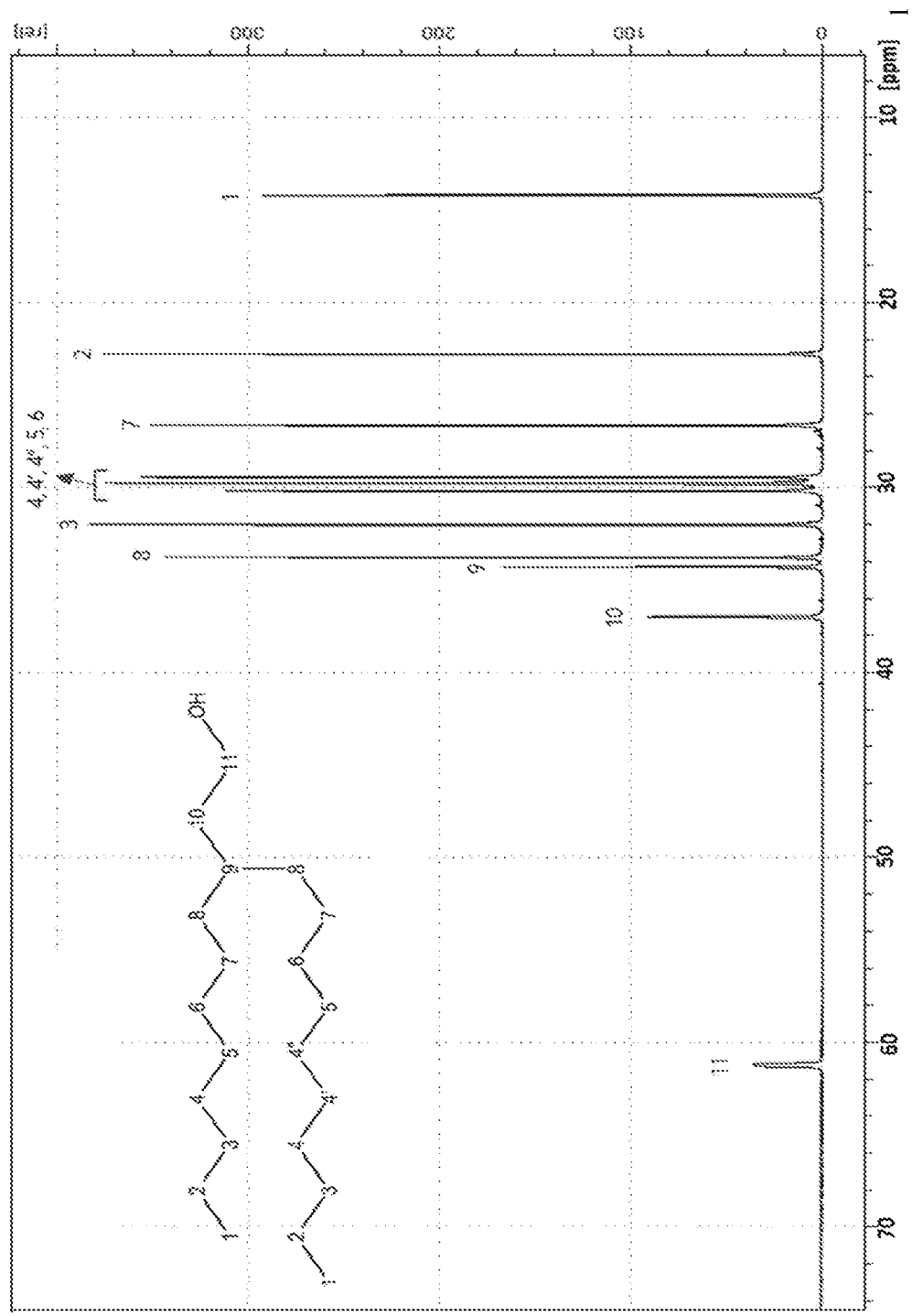
FIG. 1 is a 13C-NMR spectra of the C21-alcohol made in Example B1 in this disclosure.

In this disclosure, the indefinite article "a" or "an" means at least one, unless it is clearly specified or indicated by the context to mean one.

The term "alkyl group" or "alkyl" interchangeably refers to a saturated hydrocarbyl group consisting of carbon and hydrogen atoms. "Linear alkyl group" refers to a non-cyclic alkyl group in which all carbon atoms are covalently connected to no more than two carbon atoms. "Branched alkyl group" refers to a non-cyclic alkyl group in which at least one carbon atom is covalently connected to more than two carbon atoms. "Cycloalkyl group" refers to an alkyl group in which all carbon atoms form a ring structure comprising one or more rings.

The term "aryl group" refers to an unsaturated, cyclic hydrocarbyl group consisting of carbon and hydrogen atoms in which the carbon atoms join to form a conjugated π system. Non-limiting examples of aryl groups include phenyl, 1-naphthyl, 2-naphthyl, 3-naphthyl, and the like.

The term "arylalkyl group" refers to an alkyl group substituted by an aryl group or alkylaryl group. None-limiting examples of arylalkyl group include benzyl, 2-phenylpropyl, 4-phenylbutyl, 3-(3-methylphenyl)propyl, 3-(p-tolyl)propyl, and the like.

The term "alkylaryl group" refers to an aryl group substituted by an alkyl group. Non-limiting examples of alkylaryl group include 2-methylphenyl, 3-methylphenyl, 4-methylphenyl, 2-methyl-1-naphtyl, 6-phenylhexyl, 5-pentylphenyl, 4-butylphenyl, 4-terterybutylphenyl, 7-phenylheptanyl, 4-octylphenyl, and the like.

The term "cycloalkylalkyl group" refers to an alkyl group substituted by a cycloalkyl group or an alkylcycloalkyl group. An example of cycloalkylalkyl group is cyclohexylmethyl.

The term "alkylcycloalkyl group" refers to a cycloalkyl group substituted by an alkyl group. Non-limiting examples of alkylcycloalkyl group include 2-methylcyclohexyl, 3-methylcyclohexyl, 4-methylcyclohexyl, 4-tertiary butyl cyclohexyl, 4-phenylcyclohexyl, cyclohexylpentyl, and the like.

The term "Hydrocarbyl group" or "hydrocarbyl" interchangeably refers to a group consisting of hydrogen and carbon atoms only. A hydrocarbyl group can be saturated or unsaturated, linear or branched, cyclic or acyclic, containing a cyclic structure or free of cyclic structure, and aromatic or non-aromatic.

"Cn" group or compound refers to a group or a compound comprising carbon atoms at total number thereof of n. Thus, "Cm-Cn" or "Cm to Cn" group or compound refers to a group or compound comprising carbon atoms at a total number thereof in the range from m to n. Thus, a C1-C50 alkyl group refers to an alkyl group comprising carbon atoms at a total number thereof in the range from 1 to 50.

The term "carbon backbone" in an alkane or an alkyl group refers to the longest straight carbon chain in the molecule of the compound or the group in question.

The term "carbon backbone" of an olefin is defined as the straight carbon chain therein including a C=C functionality having the largest number of carbon atoms.

The term "olefin" refers to an unsaturated hydrocarbon compound having a hydrocarbon chain containing at least one carbon-to-carbon double bond in the structure thereof, wherein the carbon-to-carbon double bond does not constitute a part of an aromatic ring. The olefin may be linear, branched linear, or cyclic.

The term "terminal olefin" refers to an olefin having a terminal carbon-to-carbon double bond in the structure thereof ($(R^1R^2)$—C=CH$_2$, where $R^1$ and $R^2$ can be independently hydrogen or any hydrocarbyl group, preferably $R^1$ is hydrogen, and $R^2$ is an alkyl group). A "linear terminal olefin" is a terminal olefin defined in this paragraph wherein $R^1$ is hydrogen, and $R^2$ is hydrogen or a linear alkyl group.

The term "vinyl" means an olefin having the following formula:

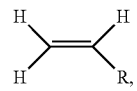

wherein R is a hydrocarbyl group, preferably a saturated hydrocarbyl group such as an alkyl group.

The term "vinylidene" means an olefin having the following formula:

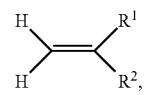

wherein $R^1$ and $R^2$ are each independently a hydrocarbyl group, preferably a saturated hydrocarbyl group such as alkyl group.

The term "1,2-di-substituted vinylene" means
(i) an olefin having the following formula:

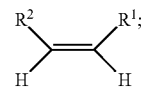

or
(ii) an olefin having the following formula:

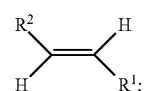

or
(iii) a mixture of (i) and (ii) at any proportion thereof, wherein $R^1$ and $R^2$, the same or different at each occurrence, are each independently a hydrocarbyl group, preferably saturated hydrocarbyl group such as alkyl group.

The term "tri-substituted vinylene" means an olefin having the following formula:

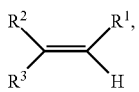

wherein $R^1$, $R^2$, and $R^3$ are each independently a hydrocarbyl group, preferably a saturated hydrocarbyl group such as alkyl group.

The term "polyalpha-olefin(s)" ("PAO(s)") includes any oligomer(s) and polymer(s) of one or more terminal olefin monomer(s). PAOs are oligomeric or polymeric molecules produced from the polymerization reactions of terminal olefin monomer molecules in the presence of a catalyst system, optionally further hydrogenated to remove residual carbon-carbon double bonds therein. Thus, the PAO can be a dimer (resulting from two terminal olefin molecules), a trimer (resulting from three terminal olefin molecules), a tetramer (resulting from four terminal olefin molecules), or any other oligomer or polymer comprising two or more structure units derived from one or more terminal olefin monomer(s). The PAO molecule can be highly regio-regular, such that the bulk material exhibits an isotacticity, or a syndiotacticity when measured by $^{13}C$ NMR. The PAO molecule can be highly regio-irregular, such that the bulk material is substantially atactic when measured by $^{13}C$ NMR. A PAO material made by using a metallocene-based catalyst system is typically called a metallocene-PAO ("mPAO"), and a PAO material made by using traditional non-metallocene-based catalysts (e.g., Lewis acids, supported chromium oxide, and the like) is typically called a conventional PAO ("cPAO"). A PAO material that has not been hydrogenated and therefore is unsaturated is called an unhydrogenated PAO ("uPAO").

NMR spectroscopy provides key structural information about the synthesized polymers. Proton NMR ($^1$H-NMR) analysis of the unsaturated PAO product gives a quantitative breakdown of the olefinic structure types (viz. vinyl, 1,2-di-substituted, tri-substituted, and vinylidene). In this disclosure, compositions of mixtures of olefins comprising terminal olefins (vinyls and vinylidenes) and internal olefins (1,2-di-substituted vinylenes and tri-substituted vinylenes) are determined by using $^1$H-NMR. Specifically, a NMR instrument of at least a 500 MHz is run under the following conditions: a 30° flip angle RF pulse, 120 scans, with a delay of 5 seconds between pulses; sample dissolved in $CDCl_3$ (deuterated chloroform); and signal collection temperature at 25° C. The following approach is taken in determining the concentrations of the various olefins among all of the olefins from an NMR spectrum. First, peaks corresponding to different types of hydrogen atoms in vinyls (T1), vinylidenes (T2), 1,2-di-substituted vinylenes (T3), and tri-substituted vinylenes (T4) are identified at the peak regions in TABLE I below. Second, areas of each of the above peaks (A1, A2, A3, and A4, respectively) are then integrated. Third, quantities of each type of olefins (Q1, Q2, Q3, and Q4, respectively) in moles are calculated (as A1/2, A2/2, A3/2, and A4, respectively). Fourth, the total quantity of all olefins (Qt) in moles is calculated as the sum total of all four types (Qt=Q1+Q2+Q3+Q4). Finally, the molar concentrations (C1, C2, C3, and C4, respectively, in mol %) of each type of olefin, on the basis of the total molar quantity of all of the olefins, is then calculated (in each case, Ci=100*Qi/Qt).

TABLE I

| Type No. | Olefin Structure | Peak Region (ppm) | Peak Area | Number of Hydrogen Atoms | Quantity of Olefin (mol) | Concentration of Olefin (mol %) |
|---|---|---|---|---|---|---|
| T1 | $CH_2=CH-R^1$ | 4.95-5.10 | A1 | 2 | Q1 = A1/2 | C1 |
| T2 | $CH_2=CR^1R^2$ | 4.70-4.84 | A2 | 2 | Q2 = A2/2 | C2 |
| T3 | $CHR^1=CHR^2$ | 5.31-5.55 | A3 | 2 | Q3 = A3/2 | C3 |
| T4 | $CR^1R^2 = CH R^3$ | 5.11-5.30 | A4 | 1 | Q4 = A4 | C4 |

The term "rhodium carbonyl compounds" means compounds comprising rhodium covalently bonded to at least one carbonyl group. Non-limiting examples of rhodium carbonyl compounds include: $Rh_4(CO)_{12}$, $Rh_6(CO)_{16}$, (acetylacetonato)dicarbonylrhodium(I), chlorodicarbonylrhodium dimer, and chlorobis(ethylene)rhodium dimer.

The term "phosphine compound" refers to a phosphorous-containing organic compound having the formula $PR_3$, where R is a hydrocarbyl group, preferably an aryl group, an alkylaryl group, an alkyl group, or an arylalkyl group.

The term "syngas" means a mixture of carbon monoxide and hydrogen, preferably at a molar ratio of 1:1.

The term "selectivity" of a terminal olefin in a reaction toward a given product species means the percentage of the terminal olefin converted into the given product species on the basis of the all of the terminal olefin converted. Thus, if in a specific oligomerization reaction, 5% of the terminal olefin monomer is converted into trimer, then the selectivity of the terminal olefin toward trimer in the oligomerization reaction is 5%.

In this disclosure, all molecular weight data are in the unit of grams per mole (g·mol$^{-1}$).

All percentages in describing chemical compositions herein are by weight unless specified otherwise. "Wt %" means percent by weight.

"Consisting essentially of" means comprising at a concentration by weight of at least 90 wt %, based on the total weight of the mixture in question. Thus, an oligomerization product mixture consisting essentially of a dimer comprises dimer at a concentration by weight of at least 90 wt %, based on the total weight of the oligomerization product mixture.

All numerical values within the detailed description and the claims herein are modified by "about" or "approximately" the indicated value, taking into account experimental error and variations that would be expected by a person having ordinary skill in the art.

All kinematic viscosity values in this disclosure are as determined pursuant to ASTM D445. Kinematic viscosity at 100° C. is reported herein as KV100, and kinematic viscosity at 40° C. is reported herein as KV40. Unit of all KV100 and KV40 values herein is cSt unless otherwise specified.

All viscosity index ("VI") values in this disclosure are as determined pursuant to ASTM D2270.

I. The Vinylidene Olefin Feed and Processes for Making the Same

I.1 General

The vinylidene olefin useful in the process of this disclosure for making the gamma-branched alcohol has a formula (F-II) below:

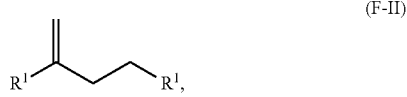
(F-II)

where each $R^1$, the same or different, can be independently any hydrocarbyl group, preferably an alkyl group, more preferably a linear or branched alkyl group, still more preferably a linear alkyl group. Preferably each $R^1$, the same or different, comprises c1 to c2 carbon atoms, where c1 and c2 can be, independently, any integer between 1 and 60, such as 1, 2, 3, 4, 5, 6, 7, 8, 9, 10, 12, 14, 16, 18, 20, 22, 24, 26, 28, 30, 32, 34, 36, 38, 40, 42, 44, 46, 48, 50, 52, 54, 56, 68, or 70, as long as c1<c2. More preferably c1=2 and c2=40. Still more preferably c1=4, and c2=30. Preferably each $R^1$, the same or different, comprises even number of carbon atoms. Particularly desirable examples of each $R^1$, the same or different, include: ethyl, n-propyl, n-butyl, n-hexyl, n-octyl, n-decyl, n-dodecyl, n-tetradecyl, n-hexadecyl, n-octadecyl, n-icosyl, n-docosyl, n-tetracosyl, n-hexacosyl, and n-octacosyl. Most preferred $R^1$ are: n-butyl, n-hexyl, n-octyl, n-decyl, and n-dodecyl, n-tetradecyl, n-hexadecyl, and n-octadecyl.

Each $R^1$, the same or different, can be a branched alkyl group, preferably a branched alkyl group having the following formula (F-IV):

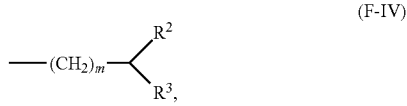
(F-IV)

where $R^2$ and $R^3$ are independently hydrocarbyl groups, preferably alkyl groups, more preferably linear or branched alkyl groups, still more preferably linear alkyl groups, m is an integer and m≥3, preferably m≥4, still more preferably m≥5, still more preferably m≥6, still more preferably m≥7. Preferably $R^2$ and $R^3$ comprises c3 to c4 carbon atoms, where c3 and c4 can be, independently, any integer between 1 and 50, such as 1, 2, 3, 4, 5, 6, 7, 8, 9, 10, 12, 14, 16, 18, 20, 22, 24, 26, 28, 30, 32, 34, 36, 38, 40, 42, 44, 46, 48, or 50, as long as c3<c4. More preferably c3=2 and c4=40. Still more preferably c3=4, and c4=30.

Preferably in the formula (F-II) of the vinylidene olefin, the two $R^1$ are identical. Thus, examples of preferred vinylidene olefin having a formula (F-II) useful in the process of this disclosure are: 3-methyleneheptane; 4-methylenenonane; 5-methyleneundecane; 7-methyleneheptadecane; 9-methylenenonadecane; 11-methylenetricosane; 13-methyleneheptacosane; and 15-methylenehentriacontane, and mixtures thereof.

Where the two $R^1$ groups in formula (F-II) differ, it is highly desirable that they differ in terms of molar mass thereof by no greater than 145 (or 130, 115, 100, 85, 70, 55, 45, 30, or even 15) grams per mole. Preferably in such cases the two $R^1$ groups differ in terms of total number of carbon atoms contained therein by no greater than 10 (or 9, 8, 7, 6, 5, 4, 3, 2, or even 1).

The vinylidene olefin having formula (F-II) can be advantageously made by dimerization of a monomer feed comprising a terminal olefin having a formula (F-III) below: $R^1$—CH=CH$_2$ (F-III). It is highly desirable that the monomer feed consists essentially of a single terminal olefin having a formula (F-III). In such case a single vinylidene olefin having a formula (F-II) where the two $R^1$ are identical can be advantageously made in the dimerization process, which can be used as the vinylidene olefin feed in step (I) of the process of this disclosure for making gamma-branched alcohol product. It is contemplated that the monomer feed may comprise multiple terminal olefins having differing formulas (F-III). In such case, as discussed below, multiple vinylidene olefins having different formulas (F-II) may be produced in the dimerization reaction, which can be used together as the vinylidene olefin feed for making a gamma-branched alcohol product comprising multiple gamma-branched alcohol compounds. Where the monomer feed comprises multiple terminal olefins, it is highly desirable that they differ in terms of molecular weight thereof by no greater than 145 (or 130, 115, 100, 85, 70, 55, 45, 30, or even 15) grams per mole. Preferably in such cases the multiple terminal olefins contained in the monomer feed differ in terms of total number of carbon atoms contained therein by no greater than 10 (or 9, 8, 7, 6, 5, 4, 3, 2, or even 1).

Such dimerization can be carried out advantageously in the presence of a catalyst system comprising a metallocene compound. U.S. Pat. No. 4,658,078 discloses a process for making a vinylidene olefin dimer from a terminal olefin monomer, the content of which is incorporated herein by reference in its entirety. The batch processes as disclosed in U.S. Pat. No. 4,658,078 resulted in the production of trimers and higher oligomers at various levels along with the intended dimer, which can be removed by, e.g., distillation, to obtain a substantially pure dimer product. The dimer product made in the batch processes of U.S. Pat. No. 4,658,078 may contain 1,2-di-substituted vinylene(s) and tri-substituted vinylenes at various levels. To the extent the concentrations of the 1,2-di-substituted vinylene(s) and tri-substituted vinylenes are acceptable to the intended application of this disclosure, the batch processes as disclosed in U.S. Pat. No. 4,658,078 may be used to produce the dimer having formula (F-II) above useful in the process for making the gamma-branched alcohol in tis disclosure.

Such dimerization can also be carried out in the presence of trialkylaluminium such as tri(tert-butyl)aluminum as disclosed in U.S. Pat. No. 4,987,788, the content of which is incorporated by reference in its entirety.

Desirably the vinylidene olefin having formula (F-II) feed used in the process of this disclosure for making gamma-branched alcohol comprises a single vinylidene olefin having formula (F-II) having a purity thereof of at least 90 wt %, preferably at least 92 wt %, more preferably at least 94 wt %, still preferably at least 95 wt %, still more preferably 96 wt %, still more preferably at least 97 wt %, still more preferably at least 98 wt %, still more preferably at least 99 wt %, based on the total weight of the olefins contained in the feed.

It is possible to use a mixture of two or more vinylidene olefins having different formulae (F-II) as the vinylidene olefin feed in the process for making a mixture of gamma-branched alcohols as the gamma-branched alcohol product. Desirably, the individual vinylidene olefins contained in the mixture have similar molecular weights, i.e., having molecular weights that differ by no more than, e.g., 145, 130, 115, 100, 85, 70, 55, 45, 30, or even 15 grams per mole. Desirably, the individual vinylidene olefins contained in the mixture differ in terms of total number of carbon atoms contained therein by no more than 10, 9, 8, 7, 6, 5, 4, 3, 2, or even 1. The individual vinylidene olefins contained in the mixture can be structural isomers. The vinylidene olefins having different chemical formulas and/or molecular weight can be converted into gamma-branched alcohol compounds having different chemical formulas and/or molecular weight under the same reaction conditions following the same reaction mechanism. As long as the mixture of gamma-branched alcohols can be used for the intended application, the corresponding mixture of vinylidene olefin can be used as the vinylidene olefin feed for making the gamma-branched alcohol product by using the process of this disclosure.

It is highly desirable that the vinylidene having formula (F-II) feed used in the process of this disclosure for making gamma-branched alcohol comprises 1,2-di-substituted vinylene(s) and tri-substituted vinylene(s) as impurities at a total concentration no greater than 5 wt %, preferably no greater than 4 wt %, still more preferably no greater than 3 wt %, still more preferably no greater than 2 wt %, still no greater than 1 wt %, based on the total weight of olefins contained in the feed.

I.2 Continuous Process for Making High-Purity Vinylidene Olefin Using a Catalyst System Comprising a Metallocene Compound However, a particularly desirable process for a vinylidene olefin dimer product from a terminal olefin feed for use in the process of this disclosure is continuous, as opposed to a batch process such as those disclosed in U.S. Pat. No. 4,658,078. The oligomerization (dimerization being one) reaction can therefore be carried out in a continuously operated reactor, such as a continuously stirred tank reactor, a plug flow reactor or a loop reactor. Quite surprisingly, it was found that in a continuous process, one can achieve an extremely high selectivity toward dimer of the terminal olefin monomer and avoid the production of high quantity of trimer and higher oligomer.

This continuous process represents a significant improvement to the processes disclosed in U.S. Pat. No. 4,658,078, as it results in the production of a high-purity vinylidene olefin dimer of the terminal olefin dimer. The oligomerization reaction pursuant to the continuous process features an exceedingly high selectivity toward dimer and exceedingly low selectivity toward trimers and higher oligomers and an exceedingly high selectivity toward vinylidene olefin dimer as opposed to 1,2-di-substituted vinylene and tri-substituted vinylene. Thus, the oligomer mixture obtained from the oligomerization step, upon removal of residual terminal olefin monomer and catalyst, can be used directly as a high-purity vinylidene olefin dimer for the process of making a gamma-branched alcohol of this disclosure. In addition, the oligomerization reaction can be carried out with a high conversion of the terminal olefin monomer. Moreover, the oligomerization reaction of the continuous process results in little isomerization of the terminal olefin monomer, the dimer, and other oligomers. Therefore, the residual terminal olefin monomer contained in the oligomerization reaction mixture can be separated and recycled to the oligomerization reaction. Last but not least, the oligomerization reaction in the continuous process is carried out under mild, steady conditions in a continuous fashion, resulting in a vinylidene olefin dimer intermediate with consistent composition and quality, which, in turn, can be used for making a gamma-alcohol product with high purity.

I.2a The Terminal Olefin

The terminal olefin monomer useful in the continuous process for making the vinylidene olefin having formula (F-II) can desirably comprise from n1 to n2 carbon atoms per molecule, where n1 and n2 can be, independently, 4, 5, 6, 7, 8, 9, 10, 12, 14, 16, 18, 20, 22, 24, 26, 28, 30, 32, 34, 36, 38, 40, 42, 44, 46, 48, 50, 52, 54, 56, 58, 60, as long as n1<n2. Preferably n1=4 and n2=50; more preferably n1=6 and n2=40; still more preferably n1=6 and n2=30; still more preferably n1=6 and n2=20.

Preferred terminal olefin monomers are mono-olefins containing one C═C bond per monomer molecule, though those olefins containing two or more C═C bonds per monomer molecule can be used as well.

The terminal olefin monomer useful in the continuous process for making the vinylidene olefin having formula (F-II) can be preferably a linear terminal olefin. Particularly useful examples of linear terminal olefins as the monomer for the process of this disclosure are: 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-icosene, 1-henicosene, 1-docosene, 1-tricosene, 1-tetracosene, 1-pentacosene, 1-hexacosene, 1-heptacosene, 1-octacosene, 1-nonacosene, and 1-triacontene. Preferred examples of linear terminal olefins as the monomer for the process of this disclosure are: 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, and 1-icosene. Still more preferred linear terminal olefin as monomer for the process of this disclosure are: 1-pentene, 1-hexene, 1-octene, 1-decene, 1-dodecene, 1-tetradecene, 1-hexadecene, 1-octadecene, and 1-icosene. Still more preferred linear terminal olefins as monomer for the process of this disclosure are: 1-hexene, 1-octene, 1-decene, 1-dodecene, 1-tetradecene, 1-hexadecene, and 1-octadecene. Linear terminal olefins having even number of carbon atoms can be advantageously manufactured by the oligomerization of ethylene, as is typically done in the industry. Many of these linear terminal olefins with even number of carbon atoms are commercially available at large quantities.

Branched terminal olefins can be used as the monomer in the process as well. Particularly useful branched terminal olefins are those represented by the following formula:

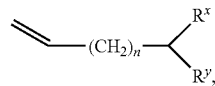

where $R^x$ and $R^y$ are independently any hydrocarbyl group, preferably any C1-C30 alkyl group, more preferably any C1-C30 linear alkyl group, n is an integer, and n≥2, preferably n≥4, more preferably n≥5. Preferably n≤30, more preferably n≤20, still more preferably n≤15.

The terminal olefin monomer may be fed as a pure material or as a solution in an inert solvent into the continuously operated oligomerization reactor. Non-limiting examples of the inert solvent include: benzene, toluene, any xylene, ethylbenzene, and mixtures thereof; n-pentane and branched isomers thereof, and mixtures thereof; n-hexane and branched isomers thereof, and mixtures thereof; cyclohexane and saturated isomers thereof, and mixtures thereof;

n-heptane and branched isomers thereof, and mixtures thereof; n-octane and branched isomers thereof, and mixtures thereof; n-nonane and branched isomers thereof, and mixtures thereof; n-decane and branched isomers thereof, and mixtures thereof; and any mixture of the above; Isopar® solvent; and the like.

The terminal olefins used herein can be produced directly from ethylene growth process as practiced by several commercial production processes, or they can be produced from Fischer-Tropsch hydrocarbon synthesis from $CO/H_2$ syngas, or from metathesis of internal olefins with ethylene, or from cracking of petroleum or Fischer-Tropsch synthetic wax at high temperature, or any other terminal olefin synthesis routes. A preferred feed for this invention is preferably at least 80 wt % terminal olefin (preferably linear alpha olefin), preferably at least 90 wt % terminal olefin (preferably linear alpha olefin), more preferably 100% terminal olefin (preferably linear alpha olefin). The feed olefins can be the mixture of olefins produced from other linear terminal olefin process containing C4 to C20 terminal olefins as described in Chapter 3 "Routes to Alpha-Olefins" of the book Alpha Olefins Applications Handbook, Edited by G. R. Lappin and J. D. Sauer, published by Marcel Dekker, Inc. N.Y. 1989.

The terminal olefin feed and or solvents may be treated to remove catalyst poisons, such as peroxides, oxygen or nitrogen-containing organic compounds or acetylenic compounds before being supplied to the polymerization reactor. The treatment of the linear terminal olefin with an activated 13 Angstrom molecular sieve and a de-oxygenate catalyst, i.e., a reduced copper catalyst, can increase catalyst productivity (expressed in terms of quantity of PAO produced per micromole of the metallocene compound used) more than 10-fold. Alternatively, the feed olefins and or solvents are treated with an activated molecular sieve, such as 3 Angstrom, 4 Angstrom, 8 Angstrom or 13 Angstrom molecular sieve, and/or in combination with an activated alumina or an activated de-oxygenated catalyst. Such treatment can desirably increase catalyst productivity 2- to 10-fold or more.

Where a substantially pure dimer compound

i.e., a vinylidene olefin having a formula (F-II) where the two $R^1$ groups are identical) is desirable, a single terminal olefin monomer ($R-CH=CH_2$) can be fed into the oligomerization reactor. Thus, a pure 1-octene feed will result in a single C16 dimer vinylidene olefin (7-methylenepentadecane), a pure 1-decene feed will result in a single C20 dimer vinylidene olefin (9-methylenenonadecane), a pure 1-dodecene feed will result in a single C24 dimer vinylidene olefin (11-methylenetricosane), a pure 1-tetradecene feed will result in a single C28 dimer vinylidene olefin (13-methyleneheptacosane).

If two different terminal olefin monomers including a first monomer ($R^a-CH=CH_2$) and a second monomer ($R^b-CH=CH_2$, where $R^b$ differs from $R^a$) are fed into the oligomerization reactor, multiple different dimer compounds may be produced at various quantities depending on the dimerization reactivity of them: a first dimer formed from two units of the first monomer

corresponding to a vinylidene olefin having a formula (F-II) where the two IV groups are identical $R^a$); a second dimer formed from two units of the second monomer

corresponding to a vinylidene olefin having a formula (F-II) where the two $R^1$ groups are identical $R^b$), and a third category of dimers formed from one unit of the first monomer and another unit of the second monomer

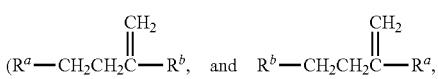

corresponding to vinylidene olefins having formula (F-II) where the two $R^1$ groups are different). The third category of dimers can have multiple isomers as shown. By way of example, a terminal olefin feed consisting of 1-decene and 1-dodecene in the continuous process for making the vinylidene olefin having formula (F-II) results in the production of a dimer mixture comprising 9-methylenenonadecane, 9-methylenehenicosane, 11-methylenehenicosane, and 11-methylenetricosane. To the extent such a dimer mixture is acceptable for the intended application, a mixture of two (or even more) terminal olefin may be used as a terminal olefin feed into the oligomerization reactor. In commercial productions, even a high-purity terminal olefin feed invariably contains impurities such as other terminal olefins at various concentrations in addition to the predominant terminal olefin. As a result, various quantities of multiple minor vinylidene olefin dimer olefins may be produced in addition to the intended predominant dimer of the predominant terminal olefin. To the extent the presence of such minor vinylidene dimer olefins at the specific quantities does not interfere with the intended use of the dimer product, such terminal olefin feed comprising minor quantities of other terminal olefin(s) than the predominant terminal olefin can be tolerated in the continuous process for making the vinylidene olefin having formula (F-II).

I.2b The Metallocene Compound

The metallocene compound in the catalyst system useful in the continuous process for making the vinylidene olefin having formula (F-II) can be represented by the formula $Cp(Bg)_nMX_2Cp'$, where Cp and Cp', the same or different, represents a cyclopentadienyl, alkyl-substituted cyclopentadienyl, indenyl, alkyl-substituted indenyl, 4,5,6,7-tetrahydro-2H-indenyl, alkyl-substituted 4,5,6,7-tetrahydro-2H-indenyl, 9H-fluorenyl, and alkyl-substituted 9H-fluorenyl; Bg represents a bridging group covalently linking Cp and Cp', and n is zero (0), one (1), or two (2), preferably zero (0) or one (1), more preferably zero (0, i.e., where the metallocene compound is unbridged). Exemplary Bg can be represented by any of (i)

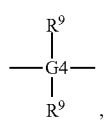

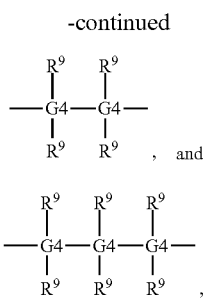

where groups G4 are, the same or different at each occurrence, independently selected from carbon, silicon, and germanium, and each $R^9$ is independently a C1-C30 substituted or unsubstituted linear, branched, or cyclic hydrocarbyl groups. Preferred $R^9$ includes substituted or unsubstituted methyl, ethyl, n-propyl, phenyl, and benzyl. Preferably Bg is category (i) or (ii) above. More preferably Bg is category (i) above. Preferably all $R^9$'s are identical.

M represents Hf or Zr. Preferably M is Zr. X, the same or different at each occurrence, independently represents a halogen such as Cl or a hydrocarbyl such as: linear or branched alkyl group such as methyl, ethyl, n-propyl, isopropyl, n-butyl and branched isomeric group thereof, n-pentyl and branched isomeric group thereof, n-hexyl and branched isomeric group thereof, n-heptyl and branched isomeric group thereof, n-octyl and branched isomeric group thereof, n-nonyl and branched isomeric group thereof, n-decyl and branched isomeric group thereof, and the like; a cycloalkyl group; a cycloalkylalkyl group; an alkylcycloalkyl group; an aryl group such as phenyl; an arylalkyl group such as benzyl; an alkylaryl group such as tolyl and xylyl. Preferably X is methyl or Cl; more preferably X is Cl. Without intending to be bound by a particular theory, it is believed that the use of the metallocene compound results in the formation of vinylidene olefin in the oligomerization reaction. A more preferred group of metallocene compound useful for the continuous process for making the vinylidene olefin used in the process for making gamma-branched alcohol product of this disclosure are those unbridged metallocene compounds having a general formula bisCpMX$_2$, where bisCp represents two cyclopentadienyl rings, M is Zr or Hf (preferably Zr), and X is as defined above, but preferably selected from Cl, C1-C10 linear or branched alkyl groups, phenyl, and benzyl. The most preferred metallocene compound useful in the continuous process for making the vinylidene olefin having formula (F-II) is bis-CpZrCl$_2$, which is commercially available and can be represented by the following formula:

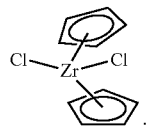

In the in the continuous process for making the vinylidene olefin having formula (F-II), the terminal olefin monomer (or multiple co-monomers) are fed into the oligomerization reactor at a first feeding rate of R(to) moles per hour, and the metallocene compound is fed into the reactor at a second feeding rate of R(mc) moles per hour. To achieve a high conversion of the terminal olefin monomer and a low selectivity of the terminal olefin toward trimer of the monomer of at most 5% (hence a high selectivity of the terminal olefin toward dimer) in the oligomerization reaction, it is highly desirable that the ratio of the first feeding rate to the second feeding rate R(to)/R(mc) be in the range from x1 to x2, where x1 and x2 can be, independently, 100, 150, 200, 250, 300, 350, 400, 450, 500, 550, 600, 650, 700, 750, 800, 850, 900, 950, or 1,000, as long as x1<x2. Preferably x1=300, and x2=800. More preferably x1=400, and x2=750. Still more preferably x1=500, and x2=750. If the ratio of R(to)/R(mc) is higher than 1,000, the conversion of the terminal olefin monomer in the oligomerization reaction can be too low. If the ratio of R(to)/R(mc) is lower than 100, the consumption of the metallocene compound can be too large, which is also undesirable.

It is highly desirable that the metallocene compound is dissolved or dispersed in an inert solvent and then fed into the reactor as a solution or a dispersion. Such inert solvent for the metallocene compound can be, e.g., benzene, toluene, any xylene, ethylbenzene, and mixtures thereof; n-pentane and branched isomers thereof, and mixtures thereof; n-hexane and branched isomers thereof, and mixtures thereof; cyclohexane and saturated isomers thereof, and mixtures thereof; n-heptane and branched isomers thereof, and mixtures thereof; n-octane and branched isomers thereof, and mixtures thereof; n-nonane and branched isomers thereof, and mixtures thereof; n-decane and branched isomers thereof, and mixtures thereof; and any mixture of the above; Isopar® solvent; and the like.

One or more metallocene compound(s) may be used in the continuous process for making the vinylidene olefin having formula (F-II).

I.2c The Alumoxane

The alumoxane used in the process of this disclosure functions as activator of the metallocene compound and scavenger for impurities (such as water). Alumoxanes can be obtained by partial hydrolysis of alkyl aluminum compounds. Thus, non-limiting examples of alumoxanes useful in the process of this disclosure include those made by partial hydrolysis of trimethyl aluminum, triethyl aluminum, tri(n-propyl)aluminum, tri(isopropyl)aluminum, tri(n-butyl) aluminum, tri(isobutyl)aluminum, tri-(tert-butyl)aluminum, tri(n-pentyl)aluminum, tri(n-hexyl)aluminum, tri(n-octyl) aluminum, and mixtures thereof. Preferred alumoxane for the process of this disclosure is methylalumoxane ("MAO") made from partial hydrolysis of trimethyl aluminum.

The alumoxane feed supplied into the continuously operated oligomerization reactor is advantageously substantially free of metal elements other than aluminum, alkali metals, alkaline earth metals, and the metal(s) contained in the metallocene compound(s) described above. Preferably, the alumoxane feed used in the process of this disclosure comprises metal elements other than aluminum, alkali metals, alkaline earth metals, Zr, and Hf at a total concentration of no greater than x1 ppm by mole, based on the total moles of all metal atoms in the alumoxane feed, where x1 can be 50,000, 40,000, 30,000, 20,000, 10,000, 8,000, 6,000, 5,000, 4,000, 2,000, 1,000, 800, 600, 500, 400, 200, 100, 80, 60, 50, 40, 20, or even 10. More preferably, the alumoxane feed used in the process of this disclosure comprises metal elements other than aluminum, Zr, and Hf at a total concentration of no greater than x2 ppm by mole, based on the total moles of all metal atoms in the alumoxane feed, where x2 can be 50,000, 40,000, 30,000, 20,000, 10,000, 8,000, 6,000, 5,000, 4,000, 2,000, 1,000, 800, 600, 500, 400, 200, 100, 80, 60, 50, 40, 20, or even 10. Still more preferably, the alumoxane feed fed into the reactor is free of all metals other than aluminum and the metal(s) contained in the metallocene compound(s) described above. Ions or compounds of metal elements other than aluminum, alkali metals and alkaline earth metals can be Lewis acids capable of catalyzing undesired polymerization of the terminal olefin monomer, the dimer and higher oligomers, resulting in the production of undesired 1,2-di-substituted vinylenes and tri-substituted vinylenes. Lewis acids such as metal ions can also catalyze the isomerization of the terminal olefin monomer and the isomerization of the vinylidene olefin dimer and higher oligomers, resulting in the production of internal olefin isomers of the terminal olefin monomer, 1,2-di-substituted vinylene and tri-substituted vinylene dimers and higher oligomers, which is undesirable for many applications of the oligomer product, including but not limited to the dimer product.

Preferably the alumoxane used in the continuous process for making the vinylidene olefin having formula (F-II) is substantially free of any Lewis acid capable of catalyzing the isomerization of the terminal olefin monomer, isomerization of a vinylidene olefin dimer, and polymerization of the terminal olefin monomer via mechanism differing from the oligomerization catalyzed by the metallocene compound used herein. For the purpose of this disclosure, the metallocene compound per se, the alumoxane per se, and any variations and derivatives thereof during the oligomerization reaction are not considered as Lewis acids.

A portion or the entirety of the alumoxane fed into the continuously operated oligomer reactor may be mixed with a portion or the entirety of the metallocene compound(s) described above, preferably dissolved and/or dispersed into an inert solvent, before it is fed into the reactor. In such case, the stream carrying a portion or the entirety of alumoxane fed into the reactor may contain the metal element(s) contained in the metallocene compound(s).

The alumoxane may be supplied into the reactor as a stream separate from the terminal olefin monomer stream and the metallocene compound stream. Alternatively or in addition, at least a portion of the alumoxane may be combined with the terminal olefin monomer and supplied into the reactor together. Mixing alumoxane with the olefin monomer before being supplied into the reactor can result in the scavenging of catalyst poisons contained in the monomer feed before such poisons have a chance to contact the metallocene compound inside the reactor. It is also possible to combine at least a portion of the alumoxane with at least a portion of the metallocene compound in a mixture, and supply the mixture as a catalyst stream into the reactor.

The alumoxane is desirably dissolved or dispersed in an inert solvent before being fed into the reactor or before being combined with the monomer feed and/or the metallocene compound. Mention of non-limiting examples of such inert solvent can be made of the following: benzene, toluene, any xylene, ethylbenzene, and mixtures thereof; n-pentane and branched isomers thereof, and mixtures thereof; n-hexane and branched isomers thereof, and mixtures thereof; cyclohexane and saturated isomers thereof, and mixtures thereof; n-heptane and branched isomers thereof, and mixtures thereof; n-octane and branched isomers thereof, and mixtures thereof; n-nonane and branched isomers thereof, and mixtures thereof; n-decane and branched isomers thereof, and mixtures thereof; and any mixture of the above; Isopar® solvent; and the like.

I.2d Oligomerization Reaction Conditions

In the continuous process for making the vinylidene olefin having formula (F-II), the terminal olefin monomer (or multiple co-monomers) is fed into the oligomerization reactor at a first feeding rate of R(to) moles per hour, and the metallocene compound is fed into the reactor at a second feeding rate of R(mc) moles per hour, and the alumoxane is fed into the reactor at a third feeding rate corresponding to R(Al) moles of aluminum atoms per hour.

To achieve a high conversion of the terminal olefin monomer and a low selectivity of the terminal olefin toward trimer of the monomer of at most 5% (hence a high selectivity of the terminal olefin toward dimer) in the oligomerization reaction, it is highly desirable that the ratio of the third feeding rate to the second feeding rate R(Al)/R(mc) be in the range from y1 to y2, where y1 and y2 can be, independently, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, as long as y1<y2. Preferably y1=2.0, and y2=12.0. More preferably y1=2.0, and y2=10.0. Still more preferably y1=2.0, and y2=7.0. Still more preferably y1=2.0, and y2=5.0. If the ratio of R(Al)/R(mc) is higher than 15.0, selectivity of the terminal olefin toward trimer and higher oligomers can be too high. If the ratio of R(Al)/R(mc) is lower than 1.0, the conversion of the terminal olefin monomer in the oligomerization reaction can be too low.

The oligomerization reaction in the process of this disclosure advantageously is carried out at a mild temperature in the range from t1 to t2° C., where t1 and t2 can be, independently, 30, 35, 40, 45, 50, 55, 60, 65, 70, 75, 80, 85, or 90, as long as t1<t2. Preferably t1=40, and t2=80. More preferably t1=50, and t2=75. If the temperature is below 30° C., the reaction kinetics can be too slow. If the temperature is higher than 90° C., selectivity of the terminal olefin toward trimer and higher oligomers can be too high and the catalyst activity may be too low.

The oligomerization reaction may be carried out at a residence time in the range from rt1 to rt2 hours, where rt1 and rt2 can be, independently, 1.0, 1.5, 2.0, 2.5, 3.0, 3.5, 4.0, 4.5, 5.0, 5.5, 6.0, 6.5, 7.0, 7.5, 8.0, 8.5, 9.0, 9.0, 10, 12, 15, 18, 24, 30, 36, 42, or 48, as long as rt1<rt2. Preferably rt1=3 and rt2=8. More preferably rt1=4 and rt2=8. Still more preferably rt1=5 and rt2=7.

The oligomerization reaction is preferably carried out in the presence of mechanical stirring of the reaction mixture such that a substantially homogeneous reaction mixture with a steady composition is withdrawn from the reactor once the reactor reaches steady state.

Advantageously the oligomerization reaction of the process of this disclosure is carried out under mild pressure. Because the oligomerization reaction is sensitive to water and oxygen, the reactor is typically protected by an inert gas atmosphere such as nitrogen. To prevent air leakage into the reactor, it is desirable that the total pressure inside the reactor is slightly higher than the ambient pressure.

The oligomerization reaction can be carried out in the presence of a quantity of inner solvent. Non-limiting examples of such solvent include: benzene, toluene, any xylene, ethylbenzene, and mixtures thereof; n-pentane and branched isomers thereof, and mixtures thereof; n-hexane and branched isomers thereof, and mixtures thereof; cyclohexane and saturated isomers thereof, and mixtures thereof; n-heptane and branched isomers thereof, and mixtures thereof; n-octane and branched isomers thereof, and mixtures thereof; n-nonane and branched isomers thereof, and mixtures thereof; n-decane and branched isomers thereof, and mixtures thereof; and any mixture of the above; Isopar® solvent; and the like.

Due to the nature of the metallocene compound and the alumoxane used in the process of this disclosure, in the oligomerization reaction, a high selectivity of the terminal olefin toward vinylidenes olefins (e.g., at least 95%, 96%, 97%, 98%, or even 99%) and a low selectivity of the terminal olefin toward internal olefins including 1,2-di-substituted vinylenes and tri-substituted vinylenes (e.g., at most 5%, 4%, 3%, 2%, or even 1%) can be achieved. Thus, the oligomers thus made, especially the dimer, tend to be predominantly vinylidene and can be advantageously used as a vinylidene without further purification in applications where vinylidenes are desired.

As a result of the use of a continuous process, and the use of a metallocene compound and an alumoxane in the respective quantities above, we were able to achieve extremely low selectivity of the terminal olefin of the terminal olefin monomer toward trimer in the oligomerization reaction of at most 5%, thereby achieving a high selectivity of the terminal olefin toward the intended dimer. In certain embodiments, selectivity of the terminal olefin toward trimer can reach no greater than 4%, no greater than 3%, no greater than 2%, or even no greater than 1%. At such low selectivity of the terminal olefin toward trimer, selectivity of the terminal olefin toward tetramer and even higher oligomers are even lower and in many embodiments negligible. Thus, in the oligomerization reaction of the process of this disclosure, the selectivity of the terminal olefin toward tetramer and higher oligomers is typically no greater than 2%, or no greater than 1%, or no greater than 0.5%, or even no greater than 0.1%. Thus, in the oligomerization reaction of the process of this disclosure, the selectivity of the terminal olefin toward dimer can be at least 90% (or ≥91%, ≥92%, ≥93%, ≥94%, ≥95%, ≥96%, ≥97%, ≥98%, or even ≥99%).

In addition to the high selectivity of the terminal olefin monomer toward dimer in the oligomerization reaction, the process of this disclosure also exhibits a high conversion of the terminal olefin monomer, e.g., a conversion of at least 40%, 45%, 50%, 55%, 60%, 65%, or 70%, can be achieved in a single pass oligomerization reaction. With recycling of unreacted monomer separated from the oligomerization reaction mixture to the oligomerization reactor, the overall conversion can be even higher, making the process of this disclosure particular economic.

Because the alumoxane introduced into the reaction system in the process of this disclosure is substantially free of metals other than aluminum, metals contained in the metallocene compound, alkali metals, and alkaline earth metals, the terminal olefin monomer does not undergo significant isomerization reaction. Likewise, the isomerization of the vinylidene dimers and higher oligomers to form 1,2-di-substituted vinylene and tri-substituted vinylene is substantially avoided as well.

I.2e Post-Oligomerization Treatment

The oligomerization reaction mixture stream withdrawn from the reactor typically comprises the unreacted terminal olefin monomer, the intended dimer, trimer, tetramer and higher oligomers, the metallocene compound, the alumoxane, and optional solvent.

Once the oligomerization reaction mixture stream leaves the reactor, typically a stream of quenching agent is injected into the stream to terminate the oligomerization reactions. Non-limiting examples of quenching agents include: water, methanol, ethanol, CO2, and mixtures thereof. A particularly desirable quenching agent is water.

The metal elements contained in the oligomerization mixture, including aluminum and Zr or Hf, needs to be removed from the mixture. Removal thereof can be achieved through mechanical filtration using a filtration aid such as Celite. Presence of aluminum in the liquid mixture can cause isomerization of the monomer and dimer during subsequently processing steps, such as distillation to remove the unreacted monomers and the optional distillation to remove higher oligomers such as trimers and tetramers in rare cases where the purity requirement for the dimer is so high that even the small quantity of trimer and higher oligomers produced in the continuous process for making the vinylidene olefin having formula (F-II) is considered excessive. It is highly desirable that upon filtration, the liquid mixture contains aluminum at a concentration no higher than 50 ppm by weight (preferably no higher than 30 ppm, still more preferably no higher than 20 ppm, still more preferably no higher than 10, still preferably no higher than 5 ppm), based on the total weight of the liquid mixture.

Upon filtration, a mixture comprising monomer, the desired dimer, the trimer and higher oligomers and the optional solvent is obtained. The monomer and solvent can be removed by flashing or distillation at an elevated temperature and/or optionally under vacuum. Because isomerization of the monomer is avoided in (i) in the oligomerization reaction due to the lack of Lewis acid capable of catalyzing isomerization reaction and (ii) in the flashing/distillation step due to the removal of aluminum and other metal elements from the liquid mixture at the earlier filtration step, the monomer reclaimed form the mixture consists essentially of the terminal olefin monomer as introduced into the reactor. As such, the reclaimed monomer can be recycled to the oligomerization reactor as a portion of the monomer stream. The thus obtained oligomer mixture absent monomer and solvent may be used as a vinylidene dimer olefin product as is due to the low percentage of trimer and higher oligomers. For certain applications where even higher purity of the dimer is desirable, one can remove the timer and higher oligomers by further separation such as distillation.

I.2f The Vinylidene Dimer Product

The dimer product as a result of the continuous process for making the vinylidene olefin having formula (F-II) advantageous comprises dimer(s) of the monomer(s) as the predominant component, and trimers at a concentration no higher than 5 wt % (preferably ≤4 wt %, ≤3 wt %, ≤2 wt %, ≤1 wt %, or even ≤0.5 wt %), based on the total weight of the dimer product. Advantageously, the dimer product comprises dimer at a concentration of at least 90% (or ≥91%, ≥92%, ≥93%, ≥94%, ≥95%, ≥96%, ≥97%, ≥98%, or even ≥99%), based on the total weight of the dimer product.

The dimer product as a result of the continuous process for making the vinylidene olefin having formula (F-II) can advantageous comprise vinylidene(s) at a total concentration of at least 95 wt % (preferably ≥96 wt %, ≥97 wt %, ≥98%, or even ≥99 wt %), based on the total weight of the dimer product.

The vinylidene dimer product obtainable from the process of this disclosure can advantageously comprise one of the following compounds at a concentration of at least 95 wt %, at least 96 wt %, at least 97 wt %, at least 98 wt %, or even at least 99 wt %, based on the total weight of the dimer product, if a substantially pure terminal olefin (with a concentration of at least 95 wt %, 96 wt %, 97 wt %, 98 wt %, or 99 wt % of the terminal olefin, based on the total weight of the terminal olefins included in the monomer feed) is utilized as the monomer feed: 3-methylenepentane (from 1-butene); 4-methylenenonane (from 1-pentene); 5-methyleneundecane (from 1-hexene); 6-methylenetridecane (from 1-heptene); 7-methylenepentadecane (from 1-octene); 8-methyleneheptadecane (from 1-nonene); 9-methylenenonadecane (from 1-decene); 11-methylenetricosane (from 1-dodecene); 13-methyleneheptacosane (from 1-tetradecene); 15-methylenehentriacontane (from 1-hexadecene); 17-methyleneheptatriacontane (from 1-octadecene); and 19-methylenenonatriacontane (from 1-iscocene).

The high-purity, predominantly dimer, predominantly vinylidene product resulting from the continuous process for making the vinylidene olefin having formula (F-II) can then be advantageously used as is as a high-purity organic compound in many applications, including in the hydroformylation reaction to make the gamma-branched alcohol in this disclosure.

II. Hydroformylation of the Vinylidene Olefin Feed to Make the Gamma-Branched Alcohol Product U.S. Pat. No. 8,383,869 B2 discloses a process for making gamma-branched alcohols from a terminal olefin including a first step of producing a vinylidene dimer of the terminal olefin, followed by hydroformylation of the vinylidene dimer. This patent teaches that in the hydroformylation process, multiple alcohol isomers will be produced (lines 30-36, column 4). Because the isomers have the same molecular weight and similar molecular structure, it follows from the teaching in U.S. Pat. No. 8,383,869 that it would be very difficult to produce one gamma-branched alcohol at high purity by hydroformylation of a vinylidene olefin. JP2005-298443A discloses a similar process for making gamma-branched alcohols from alpha-olefin. While a high purity of a gamma-branched alcohol was reportedly produced in an example in this patent publication by using a cobalt-containing carbonylation catalyst, the purity still has room for improvement. In addition, the overall yield of the gamma-branched alcohol product from the terminal olefin as disclosed in JP2005-298443A has room for improvement as well.

The present inventors have surprisingly found that by using a Rh-containing carbonylation catalyst in combination with a phosphine compound, one can produce gamma-branched alcohols having formula (F-I) at an exceedingly high selectivity, significantly higher than that disclosed in JP2005-298443A, and contrary to the teaching in U.S. Pat. No. 8,383,869.

II.1 The Rh-Containing Compound

In the carbonylation step, the vinylidene olefin molecule reacts with CO and H2 to product a carbonylated derivative of the vinylidene. Without intending to be bound by a particular theory, it is believed that an aldehyde is formed as a result.

Examples of the Rh-containing compound include the following of rhodium at any oxidative state (e.g., (I), (II) or (III)) and mixtures thereof: oxides; inorganic salts such as rhodium fluoride, rhodium chloride, rhodium bromide, rhodium iodide, rhodium nitrate, and rhodium sulfate; rhodium salts of carboxylic acids such as rhodium acetate, di-rhodium tetracetate, rhodium acetylacetonate, rhodium(II) isobutyrate, rhodium(II) 2-ethylhexanoate; rhodium carbonyl compounds such as $Rh_4(CO)_{12}$, $Rh_6(CO)_{16}$, (acetylacetonato)dicarbonylrhodium(I), chlorodicarbonylrhodium dimer, chlorobis(ethylene)rhodium dimer, hexarhodiumhexadecylcarbonyl, tetrarhodiumdodecylcarbonyl, and the like.

Exemplary catalytically effective amount of the Rh-containing compound can range from n1 to n2 micromoles of the Rh-containing compound per mole of the vinylidene olefin to be converted, where n1 and n2 can be, independently, 200, 250, 300, 350, 400, 450, 500, 550, 650, 700, 750, 800, 850, 900, 950, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, or 3,000, as long as n1<n2. Preferably n1=300 and n2=2500. More preferably n1=500 and n2=2,000. Still more preferably n1=600, and n2=1,800.

A portion of the Rh-containing compound can be solubilized in an inert solvent, or dispersed in an inert liquid medium and then introduced into the reaction system. Alternatively or additionally, a portion of the Rh-containing compound can be dispersed in the vinylidene olefin to be converted as a suspension to effect the catalytic effect. In the latter case, it is highly desirable that the reactor is equipped with a mechanical stirrer, such that the reaction is conducted with continuous stirring to achieve a uniform distribution of the Rh-containing compound in the reaction media.

Cobalt-containing compounds were used previously to catalyze the carbonylation of olefin compounds. However, in the process of this disclosure, in order to achieve a high selectivity of the vinylidene olefin toward the desired carbonylation conducive for the production of a gamma-branched alcohol, an Rh-containing compound is used instead.

II.2 The Phosphine Compound

Presence of a phosphine compound in the reaction system is important for a high selectivity toward the desired carbonylation reaction leading to a high-purity gamma-branched alcohol product having formula (F-I). As is demonstrated in the examples, Part B of this disclosure, without the presence of a phosphine compound in the reaction system, a plurality of alcohols can be produced; and on the other hand, when a phosphine compound is included, the hydroformylation is highly selective toward the desired gamma-branched alcohol having formula (F-I).

Non-limiting examples of useful phosphine compounds in the hydroformylation of vinylidene olefin in the process of this disclosure include: triphenyl phosphine; tri-(n-butyl) phosphine; tri-(tert-butyl) phosphine; tri-(n-pentyl) phosphine; tri-(n-hexyl) phosphine; tri(n-heptyl) phosphine; tri-(n-octyl) phosphine; tri(n-nonyl) phosphine; tri-(n-decyl) phosphine; and any mixture of two or more thereof, and the like.

Exemplary catalytically effective amount of the phosphine compound can range from n1 to n2 micromoles of the phosphine compound per mole of the vinylidene olefin to be converted, where n1 and n2 can be, independently, 1,000, 1,500, 2,000, 2,500, 3,000, 3,500, 4,000, 4,500, 5,000, 5,500, and 6,000, as long as n1<n2. Preferably n1=1,500 and n2=5000. More preferably n1=2,000 and n2=4,000.

Without intending to be bound by a particular theory, it is believed that the phosphine compound introduced into the carbonylation reaction mixture functions as a ligand to the Rh atom contained in the Rh-containing compound during reaction, which favorably catalyzes the desired carbonylation conducive to the formation of the gamma-branched alcohol of this disclosure when the carbonylated product from the vinylidene is reduced to produce an alcohol.

The phosphine compound may be introduced into the carbonylation reactor separately from the Rh-containing compound. Alternatively or additionally, a portion of the phosphine compound may be combined with a portion of the Rh-containing compound to form a mixture comprising a rhodium-phosphine compound complex and then the mixture is introduced in to the carbonylation reactor.

II.3 The Carbonylation Reaction

The carbonylation reaction of the vinylidene olefin is desirably conducted in the presence of an atmosphere comprising CO and hydrogen preferably at a molar ration of 1:1 at an absolute total partial pressure of CO and $H_2$ in a range from p1 to p2 MPa (million Pascal), where p1 and p2 can be, independently, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10, as long as p1<p2. Preferably p1=1.5 and p2=7.0. More preferably p1=2.0 and p2=6.0. A high total partial pressure of $CO/H_2$ is conducive to a high conversion of the vinylidene. Desirably, the conversion of vinylidene in the carbonylation reaction is at least 70%, preferably at least 80%, more preferably at least 90%, still more preferably at least 95%.

The carbonylation reaction of the vinylidene olefin is desirably conducted at a relatively mild temperature in a range from t1° C. to t2° C., where t1 and t2 can be, independently, 40, 45, 50, 55, 60, 70, 80, 90, 100, 110, 120, 130, 140, 150, 160, 170, or 180, as long as t1<t2. Preferably t1=60 and t2=150. More preferably t1=80 and t2=120. A higher temperature is conductive to a higher conversion and a higher reaction rate, but at the expense of selectivity toward the desired carbonylated compound derived from the vinylidene olefin. Reaction time can range from 0.5 hour to 96 hours, preferably 1 hour to 60 hours, more preferably no longer than 48 hours, still more preferably no longer than 36 hours, still more preferably no longer than 24 hours, still more preferably no longer than 12 hours, still more preferably no longer than 6 hours.

Given the high-pressure reaction condition, it is highly desired that the carbonylation is conducted in a batch reactor that can withstand a high internal pressure. At the end of the reaction, the reactor is cooled down and depressurized, and the carbonylation product mixture, comprising unreacted vinylidene olefin, catalyst, the desired carbonylated product, and other undesired by-products, can be advantageously reduced in the next step without the need of purification.

The carbonylation reaction of the vinylidene can be advantageously conducted with or without an inert solvent. Inert solvent useful in this step include but are not limited to: n-pentane and branched isomers thereof, and mixtures thereof; n-hexane and branched isomers thereof, and mixtures thereof; cyclohexane and saturated isomers thereof, and mixtures thereof; n-heptane and branched isomers thereof, and mixtures thereof; n-octane and branched isomers thereof, and mixtures thereof; n-nonane and branched isomers thereof, and mixtures thereof; n-decane and branched isomers thereof, and mixtures thereof; and any mixture of the above, and the like.

II.4 Reduction of the Carbonylation Product Mixture

Reduction of the carbonylated derivative (such as an aldehyde) of the vinylidene olefin obtained in the carbonylation step results in the formation of the gamma-branched alcohol having a formula (F-I).

Such reduction can be effected by combining the carbonylation product mixture (after removal of solid materials by, e.g., filtration) with a reducing agent under reducing conditions. Non-limiting examples of the reducing agent include: $NaHB_4$, $NaAlH_4$, and $LiAlH_4$.

A preferred reducing agent useful in the process of this disclosure is molecular hydrogen. Reduction by contacting hydrogen can be effected in the presence of a hydrogenation catalyst under hydrogenation conditions. The hydrogenation catalyst can advantageously comprises a hydrogenation metal such as Fe, Co, Ni, Ru, Rh, Pd, Os, Ir, Pt, and combinations thereof preferably supported on an inorganic substrate such as activated carbon, silica, alumina, and the like. Hydrogenation conditions can include a hydrogen partial pressure in a range from p3 to p4 MPa, where p3 and p4 can be, independently, 5.0, 6.0, 7.0, 8.0, 9.0, 10, 11, 12, 13, 14, 15, 16, 17, 18, 19, or 20, as long as p3<p4. Preferably p3=7 and p4=18. More preferably p3=8 and p4=15. Hydrogenation conditions can further include a hydrogenation temperature in the range from t3 to t4° C., where t3 and t4 can be, independently, 50, 60, 70, 80, 90, 100, 110, 120, 130, 140, 150, 160, 170, 180, 190, or 200, as long as t3<t4. Preferably t3=60 and t4=180. More preferably t3=70 and t4=150.

The hydrogenation reaction may be conducted with or without the presence of an inert solvent. Non-limiting examples of inert solvent useful for this step include: n-pentane and branched isomers thereof, and mixtures thereof; n-hexane and branched isomers thereof, and mixtures thereof; cyclohexane and saturated isomers thereof, and mixtures thereof; n-heptane and branched isomers thereof, and mixtures thereof; n-octane and branched isomers thereof, and mixtures thereof; n-nonane and branched isomers thereof, and mixtures thereof; n-decane and branched isomers thereof, and mixtures thereof; and any mixture of the above, and the like.

At the end of the reduction reaction, it is highly desired that substantially all of the carbonylated derivative(s) from the vinylidene olefin present in the carbonylation product mixture is converted to alcohol(s). Any olefins, including unreacted vinylidene olefin, presence in the carbonylation product mixture, are also hydrogenated into corresponding alkanes. Thus, a hydrogenation product mixture comprising the desired gamma-branched alcohol and byproducts such as alkane of the vinylidene olefin is obtained at the end of the hydrogenation reaction.

The hydrogenation product mixture can be separated to remove the light components such as alkane of the vinylidene olefin to obtain an alcohol product comprising primarily the intended gamma-branched alcohol.

In the process of this disclosure, as a result of the use of a Rh-containing carbonylation compound and the phosphine compound in the reaction system, a high selectivity of the desired gamma-branched alcohol can be achieved in the hydroformylation process, resulting in an alcohol product having a purity of the desired gamma-branched alcohol after removal of the alkane but before the removal of components heavier than the gamma-branched alcohol of at least 96 wt %, or at least 97 wt % or at least 98 wt %, or even at least 99 wt %, based on the total weight of the alcohol product.

If components heavier than the intended gamma-branched alcohol are present at quantities higher than a level acceptable for the intended application of the alcohol, one may further purify the product by using one or more of distillation, adsorption, liquid chromatography, gas chromatography, and the like, to obtain a substantially pure gamma-branched alcohol product having formula (F-I).

The combination of the hydroformylation process of this disclosure with the continuous process for making high-purity vinylidene olefin dimer of a terminal olefin monomer described in detail above can result in a high conversion, high selectivity process for making the desired gamma-branched alcohol from a terminal olefin feed and CO/H2 syngas mixture.

Commercially available terminal olefins useful in the process of this disclosure include but are not limited to: 1-butene, 1-pentene, 1-hexene, 1-octene, 1-decene, 1-dodecene, 1-tetradecene, 1-hexadecene, 1-octadecene, and the like. They can be conveniently used to fabricate gamma-branched alcohol 3-ethylheptan-1-ol, 3-propyloctan-1-ol, 3-butylnonan-1-ol, 3-hexylundecan-1-ol, 3-octyltridecan-1-ol, 3-decylpentadecan-1-ol, 3-dodecylheptadecan-1-ol, 3-tetradecylnonadecan-1-ol, 3-hexadecylhenicocan-1-ol, and 3-octadecyltricosan-1-ol, respectively.

Preferred examples of gamma-branched alcohols that can be made by the process of this disclosure include the following: 3-ethylheptan-1-ol; 3-propyloctan-1-ol; 3-butylnonan-1-ol; 3-hexylundecan-1-ol; 3-octyltridecan-1-ol; 3-decylpentadecan-1-ol; and 3-dodecylheptadecan-1-ol.

The present invention is further illustrated by the following non-limiting examples.

EXAMPLES

Part A: Dimerization of Terminal Olefins to Make Vinylidene Olefins

Example A1: Dimerization of 1-Tetradecene in a Continuous Reactor

Into a 2-gallon (6.56-liter) continuously stirred tank reactor was continuously fed 1-tetradecene feed (containing 98.6 wt % 1-tetradecene, 0.7 wt % 1-dodecene and 0.7 wt % of 1-hexadecene, and trace amounts of 1-octene and 1-decene) at a feeding rate of 3.3 moles per hour, bisCpZrCl$_2$ (dissolved or dispersed in toluene at a concentration of 1.4 wt %) at a feeding rate of 0.0048 mole per hour, and MAO (dissolved or dispersed in toluene at a concentration of 10 wt % at a feeding rate of 0.022 mole aluminum atoms per hour, operating at a constant temperature of 70° C. and residence time of 8.0 hours. The product mixture effluent exiting the reactor was immediately quenched by injecting room-temperature water at a feeding rate of 2 milliliter per hour. Filter aid was then added into the quenched product mixture. The resultant mixture was then filtered to remove solids to obtain a liquid. The liquid was then measured by gas chromatography to show a conversion of 1-tetradecene in the reaction of 71%. The liquid was then vacuum distilled at an absolute pressure of 4 mmHg (533 Pascal) to obtain a clear residual liquid as the final product. The final product was then characterized by gas chromatography to show the following composition, with total concentration of dimers at 98.84 wt %.

| Components | | Concentration (wt %) |
| --- | --- | --- |
| C14 monomer | | <0.10 |
| Dimers | C16-C26 | 1.69 |
| | C28-C32 | 97.15 |
| | C16-C32 | 98.84 |
| Trimers (C36-C48) | | 0.86 |
| Tetramers (C48-C64) | | 0.24 |

The final product was then characterized by $^1$H NMR. Data show that the final product was predominantly 13-methyleneheptacosane. Data showed the presence of vinyls, vinylidenes, 1,2-di-substituted vinylenes, and tri-substituted vinylenes. The vinyls are attributed to residual 1-tetradecene monomer. The remaining olefin types (1,2-di-substituted vinylenes, tri-substituted vinylenes, and vinylidenes) were normalized to sum up to 100%. Their respective distributions are given below:

| Olefin Type | Concentration (mol %) |
| --- | --- |
| 1,2-Di-substituted Vinylenes | 1.1 |
| Tri-substituted Vinylenes | 1.1 |
| Vinylidenes | 97.8 |

Clearly, in the CSTR process of this Example A1, a high-purity, predominantly vinylidene olefin dimer product was produced. Because of the low concentrations of heavy components such as trimers and tetramers, the final product can be used as a vinylidene olefin dimer for many applications without further distillation to remove the heavy components. The overall conversion of the monomer at 71% without recycle is quite high. The very low distribution of 1,2-di-substituted vinylenes and tri-substituted vinylenes in the final product indicates that isomerization of the vinylidene olefin dimer into either of the vinylenes occurred at an extremely low level, if at all. This is due in part to the lack of metal elements other than aluminum and zirconium that may function as a Lewis acid capable of catalyzing the isomerization of vinyls and vinylidenes to produce vinylenes. As discussed below, it is believed that the presence of metal ions such as Cu$^{2+}$ in the reaction system, which can serve as Lewis acids, can lead to dimerization of the terminal olefin through mechanism different from that catalyzed by a metallocene compound, resulting in the production of vinylenes and branched oligomers, which is highly undesirable.

Example A2: (Comparative): Dimerization of 1-Tetradecene in a Batch Reactor

Into a 2-gallon (6.56-liter) batch reactor equipped with mechanical stirring was charged 2.2 grams (0.0076 moles) bisCpZrCl$_2$ (dissolved or dispersed in toluene at a concentration of 1 wt %), followed by 1.74 grams of MAO (corresponding to 0.030 moles of aluminum atoms) dissolved or dispersed in toluene at a concentration of 10 wt %, and lastly added 4.4 kilograms (22.4 moles) of 1-tetradecene feed (containing 98.6 wt % 1-tetradecene, 0.7 wt % 1-dodecene and 0.7 wt % of 1-hexadecene, and trace amounts of 1-octene and 1-decene) over a period of 90 minutes. The reactor was then operated at a constant reaction temperature of 70° C. for a batch reaction period of 6.0 hours. The product mixture at the end of the reaction period was immediately quenched by injecting 3 grams of water. Filter aid was then added into the quenched product mixture. The resultant mixture was then filtered to remove solids to obtain a liquid. The liquid was then measured by gas chromatography to show a conversion of 1-tetradecene in the reaction to oligomers of 37%. The liquid was then vacuum distilled at an absolute pressure of 10 mmHg (1333 Pascal) to remove residual monomer and to obtain a clear residual liquid as the final product. The final product was then characterized by gas chromatography to show the following composition, with a total concentration of dimers at 95.42 wt %:

| Components | | Concentration (wt %) |
| --- | --- | --- |
| Dimers | C16-C26 | 2.19 |
| | C28-C30 | 93.23 |
| | C16-C30 | 95.42 |
| Trimers (C36-C48) | | 3.26 |
| Tetramers (C48-C64) | | 1.32 |

In the batch process of this comparative Example A2, the conversion of the linear terminal olefin monomer was much lower than in the continuous process of Example A1, even though the overall loading of the metallocene compound and MAO were comparable. In addition, the final product after the removal of residual monomer resulting from this batch process also contained trimers and tetramers at concentrations more than twice that in the final product from the continuous process of Example A1. The continuous process of Example A1 was far superior in producing a high-purity vinylidene olefin dimer product from a linear terminal olefin such as 1-tetradecene.

Example A3: (Comparative): Dimerization of 1-tetradecene in a Batch Reactor

This experiment was carried out in substantially the same manner and sequence as in comparative Example A2, with the exception that the monomer feed was added first, followed by the addition of MAO solution at the same quantity and a holding period of 1 hour, before the metallocene compound solution at the same quantity was finally added. Catalyst loadings, temperature and reaction time remained the same as in Example A2. The conversion of monomer to oligomer product was measured to be 59%, slightly higher than Example A2, but still much lower than in Example A1. The final product was measured to have the following composition:

| Components | | Concentration (wt %) |
|---|---|---|
| Dimers | C16-C26 | 1.65 |
| | C28-C30 | 84.42 |
| | C16-C30 | 86.07 |
| Trimers (C36-C48) | | 6.25 |
| Tetramers (C48-C64) | | 7.68 |

In this batch process of comparative Example A3, selectivity of the terminal olefin toward dimers in the reaction was reduced to a mere 86.07%, resulting in large quantities of trimers and tetramers in the final product, which would have to be removed by distillation in order for the dimer to be useful as a pure product for many applications.

Example A4: (Comparative): Dimerization of 1-Decene in a Batch Reactor

Into a 2-gallon (6.56-liter) batch reactor equipped with mechanical stirring was charged 5 kilograms (26 moles) of 1-decene feed (containing 98.8 wt % 1-decene, 0.5 wt % 1-octene, 0.7 wt % 1-dodecene, and trace amounts of 1-hexene and 1-tetradecene), followed by 5 grams MAO (corresponding to 0.086 moles Al atoms) dissolved or dispersed in toluene at a concentration of 10 wt %, and finally 6.3 grams (0.022 moles) bisCpZrCl$_2$ dissolved or dispersed in toluene at a concentration of 1.4 wt %, and held at a constant reaction temperature of 80° C. for a batch reaction period of 6.0 hours. The product mixture at the end of the reaction period was immediately quenched by injection of 10 grams of water. Filter aid was then added into the quenched product mixture. The resultant mixture was then filtered to remove solids to obtain a liquid. The liquid was then measured by gas chromatography to show a conversion of monomers in the reaction to oligomers of 77%. The liquid was then distilled under a vacuum of an absolute pressure of 10 mmHg (1333 Pascal) to remove residual monomer and to obtain a clear residual liquid as an intermediate product. The intermediate product was then characterized by gas chromatography to show the following composition:

| Components | Concentration (wt %) |
|---|---|
| C20 Dimers | 79.23 |
| C30 Trimer | 4.72 |
| C40 Tetramer | 16.05 |

In the batch process of this comparative Example A4, the conversion of the linear terminal olefin monomer was much lower than in the continuous process of Example A1, even though the overall loading of the metallocene compound and MAO were comparable. In addition, the intermediate product after the removal of residual monomer resulting from this batch process also contained trimers and tetramers at a concentration more than ten times that in the final product from the continuous process of Example A1. Such large quantity of trimer and tetramers render the intermediate product not useable directly as a dimer product for many applications. The continuous process of Example A1 was far superior in producing a high-purity vinylidene olefin dimer product from a linear terminal olefin.

A further step of distillation of the intermediate product was then performed to remove the heavy trimer and tetramer to obtain a final product of C20 dimer having the following composition as measured by gas chromatography:

| Component | Concentration (wt %) |
|---|---|
| C20 dimer | 99.36 |
| C30 trimer | 0.56 |
| C40 tetramer | 0.08 |

The final product in this example was characterized by 1H-NMR to determine the distribution of olefin types. Vinyls were quantified from the NMR spectra but assumed to be from residual monomer. The distribution of vinylidenes, 1,2-di-substituted vinylenes and tri-substituted vinylenes in the oligomers are as follows:

| Components | Concentration (mol %) |
|---|---|
| 1,2-Di-substituted Vinylenes | 1.2 |
| Tri-substituted Vinylenes | 0.7 |
| Vinylidenes | 98.1 |

Thus, in the batch process of this Example A4, exceedingly low distribution of 1,2-di-substituted vinylene and tri-substituted vinylene were produced. Without intending to be bound by a particular theory, it is believed that this is due to the lack of metal ions and Lewis acids other than the MAO and the metallocene compounds in the reaction system, and the hence the lack of isomerization of the terminal olefin monomer and the vinylidene olefin dimer that may be otherwise catalyzed by the presence of other Lewis acids.

U.S. Pat. No. 4,658,708 disclosed multiple examples in which a 1-olefin (such as propylene, 1-hexene, and 1-octene) was oligomerized in the presence of bisCpZrCl$_2$ and MAO to produce a dimer product with impressive selectivity toward dimers. Many examples in this patent reference showed significant isomerization of the 1-olefin to produce its isomer 2-olefin. No distribution data of the vinylidenes, 1,2-di-substituted vinylenes and tri-substituted vinylenes in the final product were given in the examples in this patent. The high level of isomerization of the 1-olefin indicates that there is a high likelihood that the vinylidene olefin dimer and higher oligomers isomerized to form 1,2-di-substituted vinylenes and tri-substituted vinylenes at significant quantities. The cause of the isomerization is highly likely the presence of CuSO$_4$ in the reaction systems, which was derived from the CuSO$_4$.5H$_2$O used for making the MAO. The Cu$^{2+}$ in CuSO$_4$, a Lewis acid, catalyzed the isomerization of the 1-olefin to form 2-olefin isomer, the isomerization of vinylidene oligomers to form 1,2-di-substituted vinylenes and tri-substituted vinylenes, and likely the polymerization of the 1-olefins by mechanism different from that catalyzed by bisCpZrCl$_2$, again resulting in the formation of 1,2-disubstituted vinylenes and tri-substituted vinylenes.

None of the examples in U.S. Pat. No. 4,658,708 used a continuous process.

Part B: Hydroformylation of Vinylidene Olefins to Make Gamma-Branched Alcohols

Example B1: Synthesis of 3-Octyltridecan-1-ol

B1a. Synthesis of 9-Methylenenonadecane

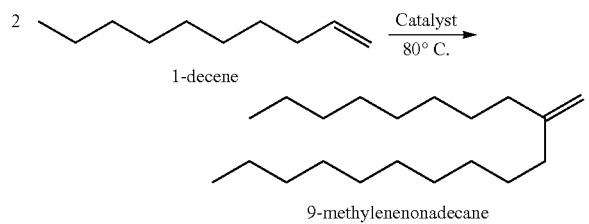

Into a batch reactor was charged 5000 grams of 1-decene (98.6% 1-decene, 0.7% 1-octene, 0.7% 1-dodecene), into which 50 grams of 10% MAO solution was added and held for 60 minutes at 80° C. 450 grams of catalyst solution (1.4 wt % biscyclopentadienyl zirconium (IV) dichloride dissolved in toluene) was subsequently added over 52 minutes. The reactor was held at 80° C. for 6 hours before the reaction was cooled and quenched with 10 mL of water. Gas chromatography showed reactor conversion was 74% with 88% selectivity to dimer and 12% selectivity to trimer and heavier species.

Filter aid was added thereafter into the fluid, which was filtered to remove Zr and/or Al-containing solid particles. The resultant mixture was then flashed to remove the residual monomer and distilled to remove heavies product to isolate the dimer species. The recovered dimer product was measured to contain dimers of the starting olefin at a concentration of 99.5 wt % by GC and a concentration of 9-methylenenonadecane at 98 mol % (by $^1$H NMR).

B1b. Synthesis of 3-Octyltridecan-1-ol by Hydroformylation in the Presence of a Rh-Containing Compound and Triphenyl Phosphine

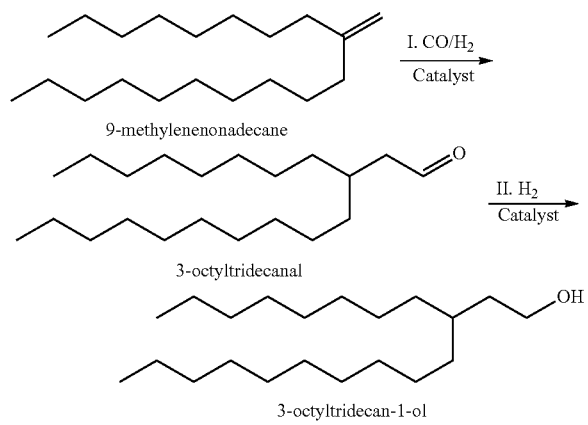

B1b-I: Carbonylation of 9-Methylenenonadecane

Into a 1-gallon autoclave equipped with mechanical stirrer, 3.24 grams of (acetylacetonato)dicarbonylrhodium and 4.87 grams of triphenyl phosphine (together "Catalyst") was mixed with 2000 grams of the 9-methylenenonadecane-containing dimer product made in step B1a above to form a slurry. The reaction system was nitrogen purged and then purged with syngas (1:1 molar ratio H$_2$:CO). The autoclave was pressurized by syngas to 510 psig (3516 kPa, gauge pressure) at 26° C., where agitation begun. Under agitation and constant pressure, temperature was then raised from 26° C. to 100° C. Syngas pressure inside the autoclave was then raised to 700 psig (4826 kPa, gauge pressure) at this temperature and held under constant pressure and temperature for 18 hours before it was depressurized. The reaction product mixture, a dark liquid, was then discharged and filtered to remove solid particles and obtain a carbonyl product mixture. Olefin conversion in this step was measured to be 92.1% with selectivity to C21 carbonyl product estimated at 99%. Infrared absorption spectra of the carbonyl product mixture with an overlay of that of the 9-methylenenonadecane-containing dimer product made in step B1a showed the formation of a peak at 1729.83 cm$^{-1}$, indicating the formation of an aldehyde.

B1b-II: Hydrogenation of the Carbonyl Product Mixture

Into a 1-gallon autoclave equipped with mechanical stirrer, the carbonyl product mixture made in step B1b-I above and 27.5 grams of Pt/C catalyst were charged to make a slurry. The autoclave was first purged three times with nitrogen. Next, the autoclave was pressured up with 100% H$_2$ to 500 psig (3447 kPa, gauge pressure) and the temperature increased to 50° C. The pressure and temperature were then slowly ramped to 100° C. and 1500 psig (10,342 kPa, gauge pressure) over 2 hours. Then, the pressure and temperature was finally increased to 150° C. and 2250 psig (15,513 kPa, gauge pressure) over one hour. The reactor was held at these conditions for 72 hours and then depressurized. The resultant slurry was filtered by vacuum filtration to obtain a crude alcohol mixture. Extent of hydrogenation was measured to be 97.9% with a yield of heavy fractions (fractions having normal boiling points higher than that of 3-octyltridecan-1-ol) at 7.9%.

B1b-III: Distillation to Obtain High-Purity 3-Octyltridecan-1-ol

Figure 2:
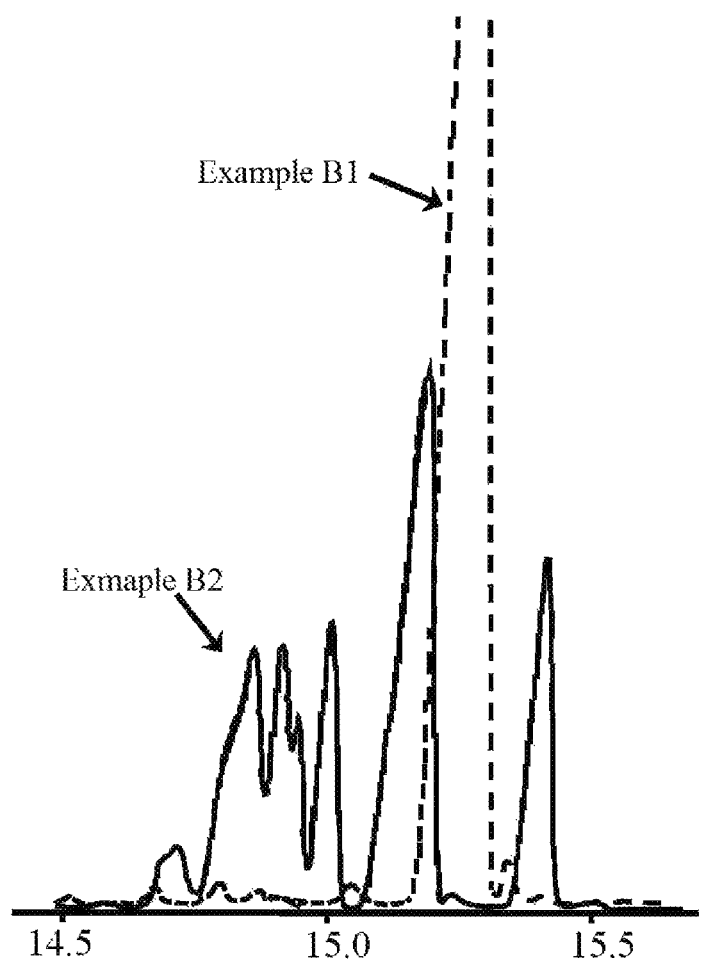
FIG. 2 is a super-imposed diagram showing and comparing portions of the gas chromatography spectra of the C21-alcohol made in Example B1 and that of the alcohol product made in Example B2.

The crude alcohol mixture produced from step B1b-II above was distilled to remove light fractions (fractions having normal boiling points lower than that of 3-octyltridecan-1-ol, such as 9-methylnonadecane) and undesired heavy fractions from the hydrogenated alcohol product to produce a high-purity fraction of 3-octyltridecan-1-ol (the "C21-alcohol"). The C21-alcohol purity was measured to be 98.2 wt %, with the balance being predominantly 9-methylnonadecane resulting from the hydrogenation in step B1b-II of the residual 9-methylenenonadecane from step B1b-I. $^{13}$C NMR of the C21-alcohol, included in FIG. 1, shows the alcohol is pure 3-octyltridecan-1-ol with a purity of higher than 99.9% based on the total weight of the alcohol product excluding 9-methylnonadecane. Gas chromatography of the C21-alcohol product produced in this step, included in FIG. 2, showed a single, tall peak, indicating a high-purity compound is included.

The C21-alcohol was measured to have the following properties: a KV100 of 4.18 cSt, a KV40 of 31.4 cSt, a viscosity index of −60.4, a flash point determined pursuant to ASTM D93 of 193° C., a density determined pursuant to ASTM D-4052 of 0.84 gram·cm$^{-3}$, and a refractive index determined pursuant to ASTM D-1218 of 1.453.

Example B2: (Comparative): Synthesis of 3-Octyltridecan-1-ol by Hydroformylation in the Presence of a Rh-Containing Compound and in the Absence of Triphenyl Phosphine Step B2a: Carbonylation of 9-methylenenonadecane in the Presence of a Rh-Containing Compound and in the Absence of Triphenyl Phosphine In a 1 gallon (3.78 liter) autoclave, 1.13 g of (acetylacetonato)dicarbonylrhodium was slurried to 2000 grams of the dimer product made in step B1a of Example B1 above. Triphenyl phosphine was not added into the reaction mixture. The reaction system was nitrogen purged and then purged with syngas (1:1 molar ratio H$_2$:CO). Pressure inside the reactor was brought up by syngas to 200 psig (1,379 kPa, gauge pressure) before increasing the temperature from 26° C. to 120° C., where the reaction continued for 16 hours. Then the reaction temperature was increased to 150° C. and pressure increased to 950 psig (6,550 kPa, gauge pressure), where the reaction continued for an additional 24 hours. The reactor was then cooled down, depressurized and the product mixture was discharged and then filtered. The carbonylation product mixture was observed to be a dark liquid. The olefin conversion was measured to be 79% with yield to carbonyl product estimated at 94% by gas chromatography.

Step B2b: Hydrogenation of the Carbonylation Product Mixture

In a 1 gallon (3.78 liter) autoclave, 25.7 grams of Pt/C catalyst was slurried into the carbonylation product mixture made in step B2a above. The reactor was then purged three times with nitrogen. The reactor was then pressured up with 100% H$_2$ to 500 psig (3447 kPa, gauge pressure) and the temperature increased to 50° C. Afterwards, the temperature was raised to 100° C. and the pressure was finally increased 2250 psig (15,500 kPa, gauge pressure). The reactor was held under these conditions for 24 hours and then cooled and depressurized. The catalyst slurry was filtered from the liquid mixture by vacuum filtration. Extent of hydrogenation was estimated to be nearly 100%. Gas chromatography showed that yield of heavy components (components having a boiling point higher than 3-octyltridecan-1-ol) was 0.8 wt %.

Step B2c: Distillation to Obtain an Alcohol Product

A batch distillation was used to remove light components and undesired heavy components to produce an alcohol product overhead. The alcohol product was measured to have a KV100 of 4.35 cSt, a KV40 of 34.2 cSt, and a viscosity index of −60.7, which are slightly different from those of the C21-alcohol in Example B1.

Gas chromatography of the alcohol product in this Example B is also provided in FIG. 2, super-imposed to the gas chromatography of the C21-alcohol product from Example B1 above. Clearly the alcohol product from this Example B2 comprises multiple compounds having similar structures and molecular weights. Without intending to be bound by a particular theory, the alcohol product from this Example B2 may comprise 3-octyltridecan-1-ol and multiple isomers thereof.

Figure 3:
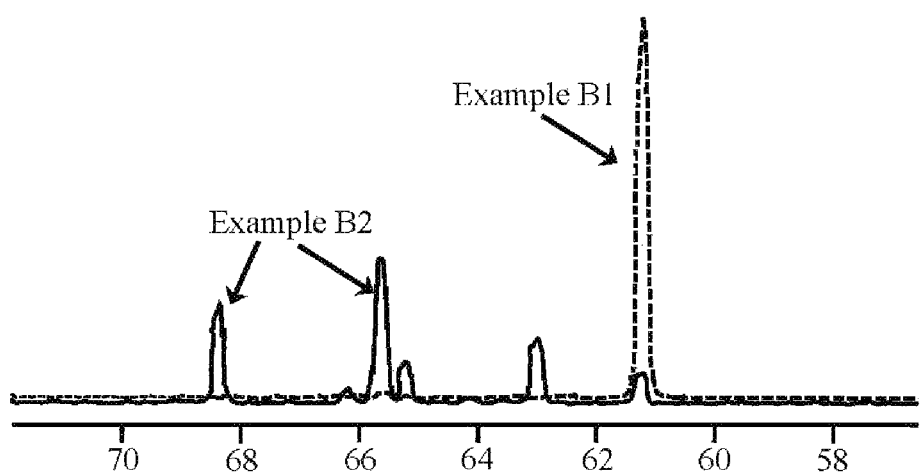
FIG. 3 is a super-imposed diagram showing and comparing portions of the 13C-NMR spectra of the C21-alcohol made in Example B1 and that of the alcohol product made in Example B2.

Portions of $^{13}$C-NMR spectra of the C21-alcohol product from Example B1 and the alcohol product from this Example B2 are super-imposed and provided in FIG. 3. It is believed that the peaks shown in FIG. 3 are for carbon atoms connected to —OH groups of the components present in the samples. Thus, from FIG. 3, it can be seen clearly that multiple alcohol compounds were present in the alcohol product of this Example B2, and essentially only one alcohol product was present in the C21-alcohol product of Example B1. In the alcohol product of this Example B2, 3-octyltridecan-1-ol (the alcohol present in the C21-alcohol product of Example B1) is present, but as a minor component.

Therefore, it is clear that in this Example B2 where no phosphine compound was included in the catalyst system, multiple alcohols were produced, and only a small portion thereof is the gamma-branched 3-octyltridecan-1-ol. Owing to structural and molecular weight similarity between the multiple alcohol species in the alcohol product of this Example B2, separation them to make a high-purity 3-octyltridecan-1-ol (such as the C21-alcohol product of Example B1) would be very difficult.

Thus, inclusion of a phosphine compound in the catalyst system in the carbonylation step of the vinylidene olefin is important for the production of a high-purity gamma-branched alcohol.

What is claimed is:

1. A process for making an alcohol product comprising a gamma-branched alcohol having a formula (F-I) below:

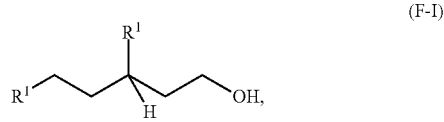

(F-I)

where each R$^1$ group, the same or different, is independently a C2 to C28 linear or branched alkyl group, the process comprising the following steps:
(I) providing a vinylidene feed comprising a vinylidene olefin having a formula (F-II) below:

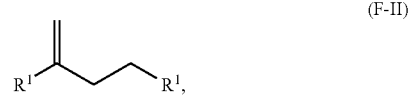

(F-II)

where the R$^1$ groups correspond to the R$^1$ groups in formula (F-I) above;
(II) contacting the vinylidene olefin with carbon monoxide and hydrogen in the presence of a carbonylation catalyst system comprising a rhodium-containing compound and a phosphine compound to obtain a carbonylation product mixture;
wherein the contacting with the carbonylation catalyst occurs at a pressure of at least 510 psig, and
(III) contacting the carbonylation product mixture with hydrogen in the presence of a hydrogenation catalyst to produce an alcohol product comprising the gamma-branched alcohol, wherein:

steps (II) and (III) combined have a selectivity of the vinylidene olefin toward the gamma-branched alcohol of at least 97%.

2. The process of claim 1, wherein the rhodium-containing compound is selected from rhodium oxides, inorganic salts of rhodium, rhodium salts of carboxylic acids, rhodium carbonyl compounds, and mixtures thereof.

3. The process of claim 1, wherein the phosphine compound is selected from triphenyl phosphine, tri-(n-butyl) phosphine; tri-(tert-butyl) phosphine; tri-(n-pentyl) phosphine; tri-(n-hexyl) phosphine; tri(n-heptyl) phosphine; tri-(n-octyl) phosphine; tri(n-nonyl) phosphine; tri-(n-decyl) phosphine; and any mixture of two or more thereof.

4. The process of claim 1, wherein in step (II), the molar ratio of carbon monoxide to hydrogen is 1:1.

5. The process of claim 1, wherein steps (II) and (III) combined have a selectivity of the vinylidene olefin toward the gamma-branched alcohol of at least 99%.

6. The process of claim 1, wherein each $R^1$ group, the same or different, is independently a linear alkyl group.

7. The process of claim 6, wherein each $R^1$ group, the same or different, is independently selected from ethyl, n-propyl, n-butyl, n-hexyl, n-octyl, n-decyl, n-dodecyl, n-tetradecyl, n-hexadecyl, n-octadecyl, n-icosyl, n-docosyl, n-tetracosyl, n-hexacosyl, and n-octacosyl.

8. The process of claim 6, wherein each $R^1$ group, the same or different, is independently selected from ethyl, n-propyl, n-butyl, n-hexyl, n-octyl, n-decyl, and n-dodecyl, n-tetradecyl, n-hexadecyl, and n-octadecyl.

9. The process of claim 1, wherein the two $R^1$ groups are identical.

10. The process of claim 1, wherein in step (I), the vinylidene feed consists essentially of a single vinylidene olefin having a formula (F-II).

11. The process of claim 1, wherein in step (I), the vinylidene feed comprises multiple vinylidene olefins each having a different formula (F-II).

12. The process of claim 11, wherein the multiple vinylidene olefins differ in terms of molecular weight thereof by no more than 150 grams per mole.

13. The process of claim 1, wherein step (I) comprises the following steps:
(Ia) providing a monomer feed comprising a terminal olefin having a formula (F-III) below:

$R^1$—CH=CH$_2$ (F-III), where $R^1$ corresponds to one of the two $R^1$ groups in formula (F-II);
(Ib) oligomerizing the monomer feed in an oligomerization reactor in the presence of a catalyst system comprising a metallocene compound to obtain an oligomerization product mixture; and
(Ic) obtaining the vinylidene feed from the oligomerization product mixture.

14. The process of claim 13, wherein in step (Ia), the monomer feed comprises a single terminal olefin having a formula (F-III).

15. The process of claim 13, wherein in step (Ia), the monomer feed comprises multiple terminal olefins having differing formula (F-III).

16. The process of claim 15, wherein in step (Ia), the multiple terminal olefins differ in terms of molecular weight thereof by no more than 100 grams per mole.

17. The process of claim 13, wherein:
in step (Ib), the metallocene compound has a formula Cp(Bg)$_n$MX$_2$Cp', wherein M is selected from Hf and Zr; each X is independently a halogen or a hydrocarbyl group; Cp and Cp', the same or different, independently represents a cyclopentadienyl, alkyl-substituted cyclopentadienyl, indenyl, alkyl-substituted indenyl, 4,5,6,7-tetrahydro-2H-indenyl, alkyl-substituted 4,5,6,7-tetrahydro-2H-indenyl, 9H-fluorenyl, and alkyl-substituted 9H-fluorenyl; each Bg is a bridging group covalently linking Cp and Cp'; and n is 0, 1, or 2; and the catalyst system further comprises an alumoxane.

18. The process of claim 17, wherein:
step (Ib) is carried out in a continuous process at a temperature in the range from 50 to 90° C.; and in step (Ib):
the metallocene compound is fed into the oligomerization reactor at a feeding rate of R(mc) moles per hour, the alumoxane is fed into the oligomerization reactor at a feeding rate of R(Al) moles per hour, the monomer is fed into the oligomerization reactor at a feeding rate of R(to) moles per hour, 350≤R(to)/R(mc)≤750, 2≤R(Al)/R(mc)≤10, an oligomer mixture comprising the vinylidene olefin and a trimer of the terminal olefin is produced, and the selectivity toward the trimer is less than 5%.

19. The process of claim 18, wherein in the metallocene compound, M is Zr.

20. The process of claim 18, wherein X is Cl.

21. The process of claim 18, wherein the alumoxane is methyl alumoxane.

22. The process of claim 18, wherein at least one of the following conditions is met:

600≤R(to)/R(mc)≤750; and

2≤R(Al)/R(mc)≤5.

23. The process of claim 18, wherein step (Ib) has a conversion of the terminal olefin of no less than 40%.

24. The process of claim 18, wherein step (Ib) has a selectivity of the terminal olefin toward the vinylidene olefin of at least 95%.

25. The process of claim 24, wherein step (Ic) does not include a step of removing a trimer of the terminal olefin from the oligomer mixture.

* * * * *